(12) United States Patent
Levy et al.

(10) Patent No.: US 11,957,558 B2
(45) Date of Patent: *Apr. 16, 2024

(54) PELVIC IMPLANTS AND METHODS OF MAKING AND USING THEREOF

(71) Applicant: LYRA MEDICAL LTD., Kerem Maharal (IL)

(72) Inventors: Gil Levy, Tel-Aviv (IL); Iram Levit, Kerem-Maharal (IL)

(73) Assignee: LYRA MEDICAL LTD., Kerem Maharal (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/665,535

(22) Filed: Feb. 6, 2022

(65) Prior Publication Data

US 2022/0160490 A1    May 26, 2022

Related U.S. Application Data

(63) Continuation of application No. 16/079,547, filed as application No. PCT/IL2017/050317 on Mar. 13, 2017, now Pat. No. 11,284,982.

(60) Provisional application No. 62/307,599, filed on Mar. 14, 2016.

(51) Int. Cl.
*A61F 2/00* (2006.01)

(52) U.S. Cl.
CPC .............. *A61F 2/0045* (2013.01); *A61F 2/00* (2013.01); *A61F 2/0036* (2013.01); *A61F 2/0063* (2013.01); *A61F 2240/001* (2013.01)

(58) Field of Classification Search
CPC .. A61F 2/0036–0077; A61F 2002/0068–0072; A61B 2017/00805
See application file for complete search history.

(56) References Cited

U.S. PATENT DOCUMENTS

| 2011/0174313 A1* | 7/2011 | von Pechmann ..... A61F 2/0063 128/834 |
| 2012/0016186 A1* | 1/2012 | Cosson ................. A61F 2/0045 600/37 |

\* cited by examiner

*Primary Examiner* — Thaddeus B Cox
(74) *Attorney, Agent, or Firm* — Momentum IP; Marc Van Dyke

(57) ABSTRACT

Pelvic implant having a frame with two arms and a sheet are disclosed. The sheet may be held under tension in the assembled implant. The implant may be planar (flat) or may be non-planar. The implant may be contoured laterally. A curved non-planar implant may be convex or concave in a rostro-caudal direction. The implants may (optionally) include two additional arms and a second sheet for supporting a urethra and/or a bladder neck. Methods for constructing and assembling the implants are disclosed. A method ultrasonically welding the frame of the implant without thermally damaging the sheet is disclosed. Methods of implantation of the implants are disclosed.

7 Claims, 15 Drawing Sheets

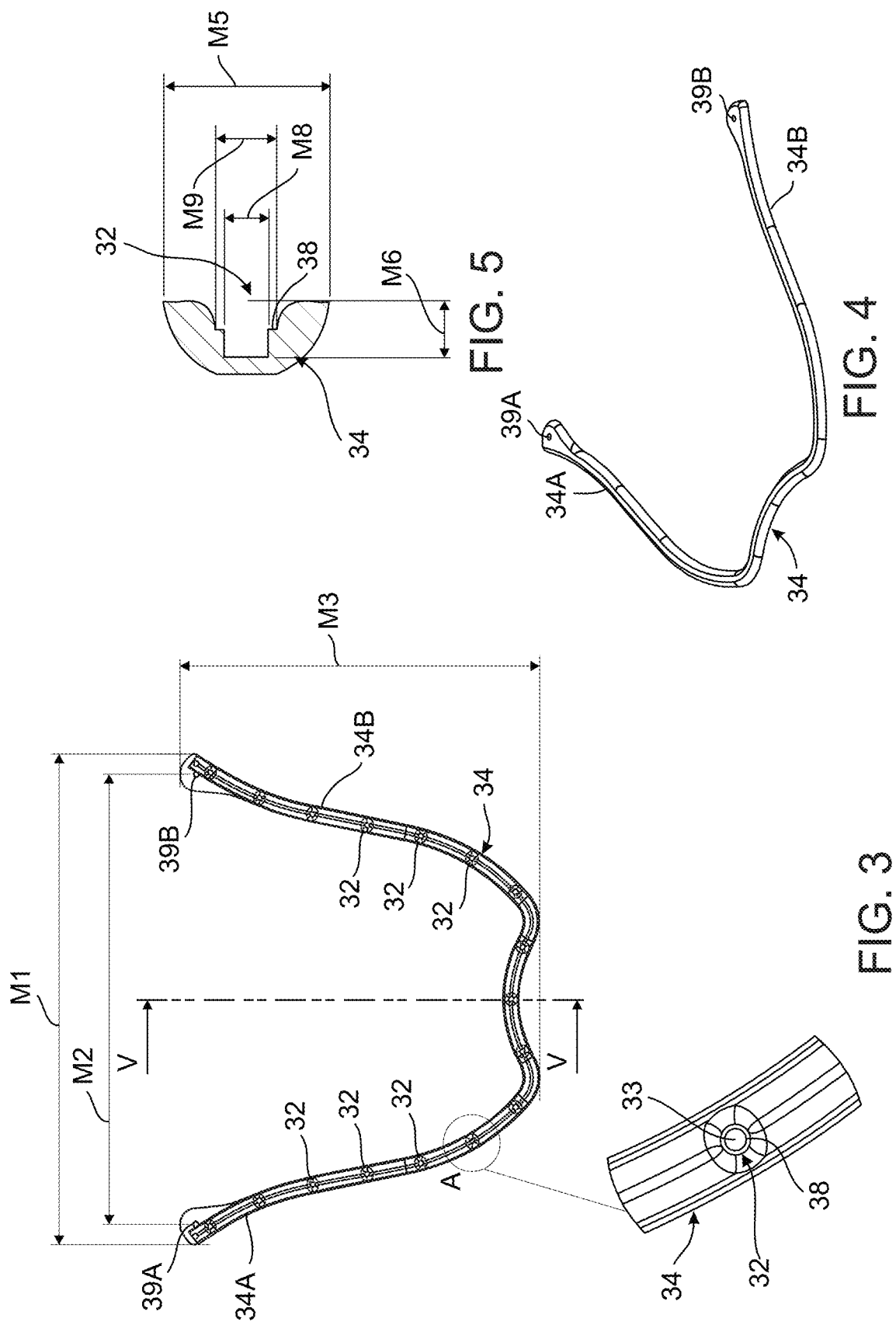

PELVIC IMPLANTS AND METHODS OF MAKING AND USING THEREOF

RELATED APPLICATION

PCT/IL2017/050317, filed on Mar. 13, 2017, is incorporated herein by reference as if fully set forth herein.

FIELD OF THE INVENTION

The present invention, in some embodiments thereof, relates to improved pelvic implants, more particularly, but not exclusively, to implants for preventing organ prolapse and to methods of constructing such implants and to methods for constructing implants suitable for other medical applications.

BACKGROUND OF THE INVENTION

Pelvic floor disorders include cystocele, rectocele, enterocele and uterine and vaginal prolapse. These disorders are often a consequence of weakness or damage to pelvic muscles and ligaments, caused by childbearing, hysterectomy, connective tissue defects, atrophy, or physical injury. Two basic approaches to remedying this condition have been the use of a removable device known as a pessary, or surgery to replace or repair parts of the pelvic supporting structures.

A pessary is a vaginal insert, having a specified geometric configuration such as, for example, a cube or a donut, which can be temporarily placed in the vaginal canal. Examples of such devices are disclosed in U.S. Pat. Nos. 6,645,137; 6,189,535, and many others.

The surgical approach includes reconstruction of the damaged support tissue using sutures or replacement of the support tissue with an implant or device. An example of such a device is disclosed in U.S. Pat. No. 6,786,861 to Pretorius. The device disclosed therein is a sling having a flexible elongate member and a distensible portion, and is configured to be inserted dorsally between the urethra and pelvic bone, with ends of the elongate member attachable to the retro-pubic area or ischial structures. Another such device is disclosed in U.S. Pat. No. 6,755,781 to Gellman. The device disclosed therein is a medical sling having one or more cuts are disposed in the material. The cuts on the sling provide open areas to permit tissue ingrowth and cross linking when the sling is implanted inside the body of the patient. These types of slings and supporting devices are configured to treat urinary incontinence rather than prolapse, and as such, they are generally located under the urethra or bladder neck.

Other devices for implantation within a pelvis are described. U.S. Pat. No. 6,592,515 to Thierfelder, for example, discloses an implant useful for a sacral colpopexy procedure for treating vaginal prolapse. The implant includes tissue engagement portions, which are configured for anchoring the implant into bone. World Publication WO 00/27304 to Ory et al. discloses a suspension device for treating prolapse and urinary incontinence, including a suspension cord, non-absorbable material, and anchoring parts which are designed to be fixed by suturing or stapling means to implanting walls.

All of these devices require suturing to anchor the device to the anatomical structures within the pelvis. Other prolapse repair kits are currently available include a frameless mesh which may be anchored to pelvic structures.

U.S. Pat. No. 7,981,024 to Levy discloses a suture-less implant for implantation within a pelvis including a frame with two arms and a connecting element connecting the two arms. A sheet or mesh is held by the frame to support pelvic organs.

There is thus an ongoing need for improved pelvic implants. There is also a need for effective methods for attaching the sheet or mesh to the frame of the implant without compromising the structural integrity and/or other physical and/or biological properties of the sheet or mesh during assembly of the implant.

SUMMARY OF THE INVENTION

The present application disclosed pelvic implants having a frame and a sheet attached to the frame. In some embodiments of the implant, the sheet is held under tension to reduce sheet erosion and/or folding after implantation. In some embodiments of the implant, the frame has two arms. In other embodiments of the implant, the frame may have four arms. In some embodiments of the implant, the implant is a non-planar implant and the frame is curved in the rostro-caudal direction such that the arms of the frame may be curved in the rostro-caudal direction. The curved arms of the frame may have a convex side and a concave side with respect to the rostro-caudal axis of the implant. In such embodiments, the curvature of the arms allow the implant to better fit the curve between the vagina and a pelvic organ (a bladder/urethra or a rectum), which advantageously reduces post implantation pain and patient discomfort. For example, in accordance with an embodiment of the implant which may be implanted between the bladder/urethra and the vagina of the female pelvis, the sides of the arms of the frame facing the bladder/urethra are convexly curved and the sides of the arms facing the vagina are concavely curved. In another embodiment of the implant, which may be implanted between the vagina and the rectum of the female pelvis, the sides of the arms of the frame facing the rectum are convexly curved and the sides of the arms facing the vagina are concavely curved. In additional embodiments of the implants (tensioned implants or non-tensioned, planar implants or curved non-planar implants), the arms may be bent at their distal ends such that a portion (or part) of the arms are bent at an angle towards each other. Other embodiments of the implant have two additional arms included in the frame such that the frame has two arms for holding the sheet or mesh and the two additional arms attached to a second (strip-like) sheet or mesh positioned to support the urethra which may advantageously prevent the urethra from kinking against the vagina after implantation. Several methods for constructing the implants are disclosed in the application, including a method for constructing the implant by ultrasonically welding the frame halves which hold the sheet or mesh between them without damaging (by softening or melting the sheet or mesh) the sheet or mesh. Additional mechanical methods for constructing the implant without the use of thermal bonding techniques are disclosed. Methods for implanting some embodiments of the pelvic implants are also disclosed in the application.

There is therefore provided, in accordance with some embodiments of the devices of the present application, a device for implantation in a pelvis, the device includes a sheet having a perimeter, and a frame including an elastic member having a first arm and a second arm. The elastic member has a compressed state and a relaxed state. The elastic member is elastically bendable to change the distance between the first arm and the second arm. The frame holds the sheet at a portion of the perimeter such that in an assembled device said sheet is held under tension.

In accordance with some embodiments of the device, the frame has contoured lateral edges.

In accordance with some embodiments of the device, the device is a flat device and the frame is flat frame.

In accordance with some embodiments of the device, the device is a curved non-planar device, the frame is a non-planar frame, and the first arm and second arm are curved to fit a curved pelvic region defined between a vagina and an organ of the pelvis.

In accordance with some embodiments of the device, the organ is a bladder and the first arm and second arm are curved to fit a curved pelvic region defined between the vagina and the bladder.

In accordance with some embodiments of the device, the organ is a rectum and the first arm and second arm are curved to fit a curved pelvic region defined between the vagina and the rectum.

In accordance with some embodiments of the device, the frame has a proximal portion and a distal portion. The first arm and the second arm each have a proximal portion and a distal portion, and the proximal portions of the first arm and second arm are bent towards each other at an angle.

In accordance with some embodiments of the device, the angle is a right angle, or an acute angle or an obtuse angle.

In accordance with some embodiments of the device, the sheet is a mesh or a sheath or a diaphragm or a membrane, or a multi-layered sheet or a divider.

In accordance with some embodiments of the device, the sheet has a substantially flat configuration.

In accordance with some embodiments of the device, the sheet has a non-planar configuration.

In accordance with some embodiments of the device, the sheet is a biocompatible sheet including a material selected from a synthetic material, a polymer based material, a biological material, a collagen, a biodegradable material, and any combinations thereof.

In accordance with some embodiments of the device, in the assembled device a restoring force applied by the first arm and the second arm to the sheet to hold the sheet under tension is in the range of 0.001-2 Newton.

In accordance with some embodiments of the device, the frame has a first configuration in which the frame is compressed, causing the sheet to be configured in a compressed position, and the frame has a second configuration in which the frame is expanded to allow the sheet to be configured in an expanded position. In the expanded position the sheet is under tension.

In accordance with some embodiments of the device, the frame includes a first half frame and a second half frame attachable to the first half frame.

In accordance with some embodiments of the device, the first half frame has multiple recesses formed in a first side of the first half frame and the second half frame has multiple protruding connecting members disposed on a first side of the second half frame. The protruding connecting members are positioned on the second half frame to match the positions of the recesses of the first half-frame.

In accordance with some embodiments of the device, the protruding connecting members are shaped to engage with a step formed in each of the multiple recesses.

In accordance with some embodiments of the device, at least some of the recesses have an open passage formed therein opening on the surface of the second side of the first half frame and the open passage is shaped to allow an end of a connecting member to protrude beyond the surface of the second side of the second half frame when a connecting member is inserted into the open passage, to allow attaching of the first and the second half frames by thermal and/or ultrasonic welding applied to the end of the connecting member protruding beyond the surface of the second side of the second half frame.

In accordance with some embodiments of the device, at least some of the recesses are shaped to receive the protruding connecting members therein and to hold the connecting members in a captive manner when the first half frame and the second half frame are aligned and pushed together.

In accordance with some embodiments of the device, the first half frame has a first side and the recesses are formed in the first side. The first half frame has a second side having a surface, and at least some of the recesses have an open passage formed therein. The open passage opens on the surface of the second side and the open passage is shaped to allow an end of a connecting member to be inserted into the open passage and to be captively held within the open passage after insertion.

In accordance with some embodiments of the device, the passage includes a first passage portion communicating with the recess and a second passage portion wider than the first passage portion and opening on the surface, and at least some of the connecting members have a slotted end to allow forcing the slotted end through the first passage portion into the second passage portion. The slotted end expands within the second passage portion to hold the connecting member captive within the second passage portion.

In accordance with some embodiments of the device, the sheet includes a first sleeve formed at a first side of the perimeter for receiving the first arm therein and a second sleeve formed on a second side of the perimeter for receiving the second arm therein.

In accordance with some embodiments of the device, the first sleeve and the second sleeve are formed by folding end portions of the sheet at the first side and at the second side and attaching at least part of the folded end portions to the surface of the sheet to form the first sleeve and the second sleeve, respectively.

In accordance with some embodiments of the device, the first and second sleeves are formed in the sheet prior to inserting the first arm and the second arm therein and the distance between the first sleeve and the second sleeve is such that the first arm and the second arm are bent towards each other prior to inserting the first arm and the second arm into the first sleeve and the second sleeve, respectively, to achieve the tensioned state of the sheet.

In accordance with some embodiments of the device, the first sleeve and said second sleeve are formed by folding portions of the perimeter of said sheet over the said first and said second arms and attaching said portions to the surface of said sheet, while said frame is in as compressed state.

In accordance with some embodiments of the device, the sheet is a first sheet. The frame also includes a third arm and a fourth arm. The device also includes a second sheet attached to the third arm and to the fourth arm for supporting a neck of a bladder and/or a urethra of the pelvis, to avoid prolapsing of the bladder and/or the urethra into the wall of a vagina of the pelvis.

In accordance with some embodiments of the device, the area of the second sheet is smaller than the area of the first sheet.

In accordance with some embodiments of the device, the first sheet is configured for implantation in the pelvis between a vagina and a bladder.

In accordance with some embodiments of the device, the first sheet is configured to be disposed between the bladder and the vagina and the second sheet is configured to be disposed between the vagina and a bladder neck and/or an urethra.

In accordance with some embodiments of the device, at least one sheet of the first sheet and the second sheet is selected from a mesh, a sheath, a diaphragm, a membrane, a divider and a multi-layer sheet.

In accordance with some embodiments of the device, at least one of the first sheet and the second is a biocompatible sheet including a material selected from a synthetic material, a polymer based material, a collagen, a biological material, a biodegradable material, and any combinations thereof.

In accordance with some embodiments of the device, at least one of the first sheet and the second sheet is an elastic sheet or a flexible sheet.

In accordance with some embodiments of the device, the frame has a first configuration in which the frame is compressed, causing the first sheet and the second sheet to be in a non-tensioned state, and said frame has a second configuration in which said frame is expanded, to allow said first sheet and said second sheet to be configured in a tensioned state.

In accordance with some embodiments of the device, the first arm, second arm, third arm and fourth arm are selected from the following:
 one or more of the first arm, second arm, third arm and fourth arm being integral portions of the frame,
 one or more of the first arm, second arm, third arm and fourth arm being an attachable part attached of the frame; and
 one or more of the first arm, second arm, third arm and fourth arm being articulated parts of the frame.

In accordance with some embodiments of the device, in the assembled device the first sheet and the second sheet are held under tension.

In accordance with some embodiments of the device, in the assembled device the first sheet is held under tension while the second sheet is not held under tension in the assembled device.

In accordance with some embodiments of the device, the in the assembled device the first sheet is held under tension while the second sheet is loose.

In accordance with some embodiments of the device, the frame includes a first half frame and a second half frame attached to each other for supporting the first sheet and the second sheet.

In accordance with some embodiments of the device, at least one of the first sheet and the second sheet is held between the first half frame and the second half frame.

In accordance with some embodiments of the device, at least one of the first sheet and the second sheet is attached to the frame by sleeves formed in the perimeter of the first sheet and/or of the second sheet.

There is also provided, in accordance with some embodiments of the devices of the present application, a device for implantation in a pelvis. The device includes a sheet having a perimeter, and an elastic frame having a first arm and a second arm for holding the sheet at a portion of the perimeter. The device is a curved non-planar device and the first arm and the second arm are curved to fit a curved pelvic region defined between a vagina and an organ of the pelvis.

In accordance with some embodiments of the device, the frame has laterally contoured edges.

In accordance with some embodiments of the device, the organ is a bladder and the first arm and second arm are curved to fit a curved pelvic region defined between the vagina and the bladder.

In accordance with some embodiments of the device, the organ is a rectum and the first arm and second arm are curved to accommodate a curved pelvic region defined between the vagina and the rectum.

In accordance with some embodiments of the device, the sheet is a first sheet and the frame also includes a third arm and a fourth arm and a the device includes a second sheet attached to the third arm and to the fourth arm for supporting a neck of a bladder and/or a urethra from prolapsing into the wall of the vagina.

In accordance with some embodiments of the device, the area of the second sheet is smaller than the area of the first sheet.

In accordance with some embodiments of the device, the first sheet is configured for implantation in said pelvis between a vagina and a bladder.

In accordance with some embodiments of the device, the first sheet is configured to be disposed between said bladder and said vagina and the second sheet is configured to be disposed between the vagina and a bladder neck and/or a urethra.

In accordance with some embodiments of the device, the second sheet is selected from a mesh, a sheath, a diaphragm, a membrane, a divider and a multi-layer sheet.

In accordance with some embodiments of the device, the second sheet is a biocompatible sheet including a material selected from a synthetic material, a polymer based material, a biological material, a collagen, a biodegradable material, and any combinations thereof.

In accordance with some embodiments of the device, the second sheet is an elastic and/or a flexible sheet.

In accordance with some embodiments of the device, the frame has a first configuration in which the frame is compressed causing the first sheet and the second sheet to be in a non-tensioned state. The frame has a second configuration in which the frame is expanded to allow the first sheet and the second sheet to be in a tensioned state.

In accordance with some embodiments of the device, the first arm, the second arm, the third arm and the fourth arm are selected from:
 one or more of the first arm, second arm, third arm and fourth arm is an integral portions of the frame,
 one or more of the first arm, second arm, third arm and fourth arm is an attachable part attached of the frame, and
 one or more of the first arm, second arm, third arm and fourth arm is an articulated part of the frame.

In accordance with some embodiments of the device, at least one of the first sheet and the second sheet is held under tension in the assembled device.

In accordance with some embodiments of the device, in the assembled device the first sheet is held under tension while the second sheet is not held under tension.

In accordance with some embodiments of the device, the frame includes a first half frame and a second half frame attached to each other for supporting the first sheet and the second sheet.

In accordance with some embodiments of the device, at least one of the first sheet and the second sheet is held between the first half frame and the second half frame.

In accordance with some embodiments of the device, at least one of the first sheet and the second sheet is attached to the frame by sleeves formed in the perimeter of at least one of the first sheet and the second sheet.

In accordance with some embodiments of the device, each of the first arm and the second arm has a proximal portion and a distal portion, wherein the proximal portions of the first arm and the second arm are bent towards each other at an angle.

In accordance with some embodiments of the device, the angle is a right angle or an acute angle or an obtuse angle.

In accordance with some embodiments of the device, the sheet is a mesh, or a sheath, or a diaphragm, or a membrane or a divider, or a multi-layered sheet.

In accordance with some embodiments of the device, the sheet is a biocompatible sheet including a material selected from a synthetic material, a polymer based material, a biological material, a biodegradable material, a collagen, and any combinations thereof.

In accordance with some embodiments of the device, the frame includes at least one elastic material.

In accordance with some embodiments of the device, in the assembled device the sheet is held under tension by the first arm and the second arm to reduce sagging of the sheet and organ prolapse after implantation.

In accordance with some embodiments of the device, the frame has a first configuration in which the frame is compressed, causing the sheet to be in a non-tensioned state. The frame has a second configuration in which the frame is expanded, to allow the sheet to be in a tensioned state, in which the sheet is under tension.

In accordance with some embodiments of the device, in the assembled device a restoring force applied by the first arm and the second arm to the sheet to hold the sheet under tension is in the range of 0.001-2 Newton.

In accordance with some embodiments of the device, the frame includes a first half frame and a second half frame attachable to the first half frame.

In accordance with some embodiments of the device, the first half frame has a plurality of recesses formed in a first side of the first half frame and the second half frame has a plurality of protruding connecting members disposed on a first side of the second half frame. The protruding connecting members are positioned on the second half frame to match the positions of the recesses of the first half-frame.

In accordance with some embodiments of the device, the protruding connecting members are shaped to engage with a step formed in each of the recesses.

In accordance with some embodiments of the device, the recesses have an open passage formed therein opening on the surface of the second side of the first half frame. The open passage is shaped to allow an end of a connecting member to protrude beyond the surface of the second side of the second half frame when a connecting member is inserted into the open passage, to allow attaching of the first and the second half frames by thermal bonding and/or ultrasonic welding applied to the end of the connecting members protruding beyond the surface of the second side of the second half frame.

In accordance with some embodiments of the device, the recesses are shaped to receive the protruding connecting members therein and to hold the connecting members in a captive manner when the first half frame and said second half frame are aligned and pushed together.

In accordance with some embodiments of the device, the first half frame has a first side, the recesses are formed in the first side, The first half frame has a second side having a surface. Each of the recesses has an open passage formed therein. The open passage opens on the surface of the second side. The open passage is shaped to allow an end of a connecting member to be inserted into the open passage and to be held in a captive manner within the open passage after insertion.

In accordance with some embodiments of the device, the passage includes a first passage portion communicating with the recess and a second passage portion wider than the first passage portion and opening on the surface. At least some of the connecting members have a slotted end to allow forcing the slotted end through the first passage portion into the second passage portion. The slotted end expands within the second passage portion to hold the connecting member captive within the second passage portion.

In accordance with some embodiments of the device, the sheet includes a first sleeve formed at a first side of the perimeter for receiving the first arm therein and a second sleeve formed on a second side of the perimeter for receiving the second arm therein.

In accordance with some embodiments of the device, the first sleeve and the second sleeve are formed by folding end portions of the sheet at the first side and at the second side of the sheet, and attaching at least part of the folded end portions to the surface of the sheet to form the first sleeve and the second sleeve.

In accordance with some embodiments of the device, the first sleeve and second sleeve are formed in the sheet prior to inserting the first arm and the second arm therein, respectively. The distance between the first sleeve and the second sleeve is such that the first arm and the second arm are bent towards each other prior to inserting the first arm and the second arm into the first sleeve and the second sleeve, respectively, for holding the sheet under tension after the first arm and the second arms are unbent.

In accordance with some embodiments of the device, the first arm and the second arm are elastically bent towards each other to reach a compressed state of the frame and wherein one or more sleeves of the first sleeve and the second sleeve is formed by folding a portion of the perimeter of the sheet over the respective arm of the first and second arms and attaching the portion to the surface of the sheet while the frame is in a compressed state and wherein the frame is relaxed into a tensioned state of the sheet.

In accordance with some embodiments of the device, the at least one of the first sleeve and the second sleeve includes both of the first sleeve and the second sleeve. The first sleeve is formed by folding a first portion of the perimeter of the sheet over the first arm and attaching the first portion to the surface of the sheet. The second sleeve is formed by folding a second portion of the perimeter of the sheet over the second arm and attaching the second portion to the surface of the sheet while the frame is in a compressed state and wherein the frame is relaxed to form a tensioned state of the sheet.

In accordance with some embodiments of the device, the area of the second sheet is smaller than the area of the first sheet.

In accordance with some embodiments of the device, the first sheet is configured for implantation in the pelvis between a vagina and a bladder.

In accordance with some embodiments of the device, the first sheet is configured to be disposed between the bladder and the vagina and the second sheet is configured to be disposed between the vagina and a bladder neck and/or a urethra.

In accordance with some embodiments of the device, the first sheet and the second sheet are selected from a mesh, a sheath, a diaphragm, a membrane, a divider and a multi-layer sheet.

In accordance with some embodiments of the device, the sheet is a biocompatible sheet including a material selected from a synthetic material, a polymer based material, a biological material, a collagen, a biodegradable material, and any combinations thereof.

In accordance with some embodiments of the device, the frame includes an elastic frame or a flexible frame.

In accordance with some embodiments of the device, the frame has a first configuration in which the frame is compressed, causing the first sheet and the second sheet to be in a tensioned state. The frame has a second configuration in which the frame is expanded, to allow the first sheet and the second sheet to be in a tensioned state.

In accordance with some embodiments of the device, the first arm, second arm, third arm and fourth arm are selected from the group of:

one or more of the first arm, second arm, third arm and fourth arm is an integral portion of the frame, one or more of the first arm, second arm, third arm, and fourth arm is an attachable part attached of the frame, and one or more of the first arm, second arm, third arm and fourth arm is an articulated part of the frame.

In accordance with some embodiments of the device, in the assembled device, at least one of the first sheet and the second sheet is held under tension.

In accordance with some embodiments of the device, in the assembled device the first sheet is held under tension while the second sheet is not held under tension.

In accordance with some embodiments of the device, the frame includes a first half frame and a second half frame attached to each other for supporting the first sheet and the second sheet.

In accordance with some embodiments of the device, at least one of the first sheet and the second sheet is held between the first half frame and the second half frame.

In accordance with some embodiments of the device, at least one of the first sheet and the second sheet is attached to the frame by sleeves formed in the perimeter of the at least one of the first sheet and the second sheet.

In accordance with some embodiments of the device, the sheet also includes or is coated with a material selected from a drug, a pharmaceutically active composition, a biologically active material, an anti inflammatory agent, an anti-bacterial agent, an anti viral agent, an antibiotic agent, a hormone, a biologically active protein, a biologically active polypeptide, a collagen, metallic ions, enzymes, enzyme precursors, biological promoters, a slow release matrix containing any therapeutic agent, and/or pharmaceutical agent and/or biologically active material, a gel matrix containing any therapeutic agent, and/or pharmaceutical agent and/or biologically active material and any combination thereof.

In accordance with some embodiments of the device, at least one of the first sheet and the second sheet also includes or is coated with a material selected from a drug, a pharmaceutically active composition, a biologically active material, an anti inflammatory agent, an anti-bacterial agent, an anti viral agent, an antibiotic agent, a hormone, a biologically active protein, a biologically active polypeptide, a collagen, metallic ions, enzymes, enzyme precursors, biological promoters, a slow release matrix containing any therapeutic agent, and/or pharmaceutical agent and/or biologically active material, a gel matrix containing any therapeutic agent, and/or pharmaceutical agent and/or biologically active material and any combination thereof.

In accordance with some embodiments of the device, the frame includes a material selected from a polymer, a metal, a biocompatible material PEEK, shape memory PEEK, polylactic acid, polyethylene glycol, a synthetic biomaterial, titanium, stainless steel, a shape-memory alloy, and any combination thereof.

In accordance with some embodiments of the device, one or more of the first arm and the second arm are selected from articulated arms, segmented arms, arms formed as an integral part of the frame, and arms that are attached to the frame.

In accordance with some embodiments of the device, one or more arms of the first arm, the second arm, the third arm and the fourth arm is selected from an articulated arm, a segmented arm, an arm formed as an integral part of said frame and an arm that is attached to said frame.

In accordance with some embodiments of the device, the device is a non-planar device, the frame is a non-planar frame and the first arm and second arm are rostro-caudally convex arms.

In accordance with some embodiments of the device, the device is a non-planar device, the frame is a non-planar frame and the first arm and the second arm are rostro-caudally concave arms.

In accordance with some embodiments of the device, the organ is a bladder and the first arm and second arm are rostro-caudally convex to fit a curved pelvic region defined between the vagina and the bladder.

In accordance with some embodiments of the device, the organ is a rectum and the first arm and second arm are rostro-caudally concave to accommodate a curved pelvic region defined between the vagina and the rectum.

There is also provided, in accordance with some embodiments of the devices of the present application, a device for implantation in a pelvis, the device includes a first sheet having a first perimeter and a second sheet having a second perimeter. The device also includes a frame for holding the first sheet at a portion of the perimeter, and for holding the second sheet at a portion of the second perimeter. The frame includes a first arm, a second arm, a third arm and a fourth arm. The first arm and the second arm hold the first sheet along at least a portion of the first perimeter and the third arm and fourth arm hold the second sheet along at least a portion of the second perimeter.

There is also provided, in accordance with the methods of the present application, a method for treating prolapse of a pelvic organ. The method includes providing any of the above described devices, compressing the frame into a first compressed configuration, introducing the device through a vagina, inserting the device into a space between the vagina and the pelvic organ, and expanding the frame into a partially relaxed configuration, in which configuration the sheet is held under tension.

In accordance with some embodiments of the methods of the present application, the expanding also includes anchoring the frame into an anatomical structure.

In accordance with some embodiments of the methods of the present application, the compressing includes elastically bending at least a portion of the frame.

In accordance with some embodiments of the methods of the present application, the expanding includes unbending at least a portion of the frame.

In accordance with some embodiments of the methods of the present application, the pelvic organ is a bladder and the inserting includes inserting the device into a space between the vagina and the bladder.

In accordance with some embodiments of the methods of the present application, the anatomical structure is a pelvic side-wall.

In accordance with some embodiments of the methods of the present application, the pelvic organ is a rectum and the inserting includes inserting the device into a space between the vagina and the rectum.

In accordance with some embodiments of the methods of the present application, the anatomical structure is a para-rectal compartment.

There is also provided, in accordance with some embodiments of the methods of the present application, a method for treating prolapse of a pelvic organ, the method includes providing any of above described devices, compressing the frame into a first compressed configuration, introducing the device through a vagina, inserting the device into a space between the vagina and the pelvic organ and expanding the frame into a second partially relaxed or fully relaxed configuration.

In accordance with some embodiments of the methods of the present application, the method also includes anchoring the frame into an anatomical structure.

In accordance with some embodiments of the methods of the present application, the compressing includes elastically bending at least a portion of the frame.

In accordance with some embodiments of the methods of the present application, the expanding includes unbending at least a portion of the frame.

In accordance with some embodiments of the methods of the present application, the inserting includes inserting the device into a space between the vagina and a bladder.

In accordance with some embodiments of the methods of the present application, the anatomical structure is a pelvic side-wall.

In accordance with some embodiments of the methods of the present application, the inserting includes inserting the device into a space between the vagina and a rectum and wherein the anatomical structure is a para-rectal compartment.

There is also provided, in accordance with some embodiments of the methods of the present application, a method for attaching a sheet to a supporting frame of an implant, the method includes providing an elastic frame having a first arm and a second arm, the frame has a relaxed configuration, a compressed configuration and a partially relaxed configuration, attaching the sheet to the frame when the frame is in the compressed configuration, and allowing the frame to relax until the relaxing of the frame is stopped by the sheet while the frame is at the partially relaxed configuration. The frame and the sheet are configured such that when the frame is in the partially relaxed configuration, the sheet is held under tension.

In accordance with some embodiments of the methods of the present application, the sheet is selected from a mesh, a single sheet, a multilayered sheet, a diaphragm, a membrane and a divider.

In accordance with some embodiments of the methods of the present application, the frame includes a first half frame and a second half frame and the attaching includes disposing the sheet between the first half frame and the second half frame and attaching the first half frame to the second half frame while the sheet is held between the first half frame and the second half frame while the first half frame and the second half frame are in a compressed configuration.

In accordance with some embodiments of the methods of the present application, the first half frame includes a plurality of recesses or through passages formed therein and the second half frame has a plurality of protruding connecting members and the attaching includes inserting the plurality of protruding connecting members through a plurality of openings formed in the sheet and into the plurality of recesses or passages of the first half frame and firmly attaching the first half frame to the second half frame.

In accordance with some embodiments of the methods of the present application, the firmly attaching is selected from mechanically attaching the first half frame to the second half frame, or thermally bonding the first half frame to the second half frame, or ultrasonically welding the first half frame to the second half frame or gluing the first half frame to the second half frame.

In accordance with some embodiments of the methods of the present application, the mechanically attaching includes attaching the first half frame to the second half frame.

In accordance with some embodiments of the methods of the present application, the attaching includes inserting the first arm into a first sleeve formed in a first portion of the perimeter and inserting the second arm into a second sleeve formed in a second portion of the perimeter.

There is also provided, in accordance with some embodiments of the methods of the present application, a method for attaching a sheet to a supporting frame of an implant, the method includes:

providing a first half frame having a plurality of recesses formed therein; providing a second half frame having a plurality of protruding connecting members disposed on the second half frame, the protruding connecting members are positioned to match the position of said recesses of the first half-frame, providing a sheet having a perimeter and a plurality of openings formed in the sheet, at least some of the openings are positioned to match the position of the protruding connecting members, inserting the plurality of protruding connecting members through the plurality of openings of the sheet into matching recesses of the plurality of recesses, and ultrasonically welding the first half-frame to the second half frame by applying ultrasonic energy to at least one of the first half frame and the second half frame to selectively melt a portion of each of the connecting members and to firmly attach the first and second half-frames to each other without thermally damaging the sheet.

In accordance with some embodiments of the methods of the present application, each of the recesses includes an open passage passing through the first half frame. The passage is configured to allow a connecting member of the connecting members to be inserted therethrough such that the end of the connecting member protrudes beyond the end of the open passage. The ultrasonic welding is performed by selectively applying ultrasonic energy to an end of each of the connecting members that protrudes beyond an open end of the passage to widen the protruding end for firmly attaching the first half frame to the second half frame without thermally damaging the sheet.

There is also provided, in accordance with some embodiments of the methods of the present application, a method for attaching a sheet to a supporting frame of an implant, the method includes the steps of: providing a first half frame having a first surface, the first half frame includes a multiple recesses formed in the first surface, providing a second half frame having a second surface including a plurality of protruding connecting members disposed on the second surface, the protruding connecting members are positioned to match the position of the recesses of the first half-frame, the connecting members and the recesses are configured such that when the connecting members are fully inserted into the recesses, the first surface and the second surface have a gap therebetween, providing a sheet having a perimeter and a plurality of openings formed in the sheet, at least some of the openings are positioned to match the position of the protruding connecting members, wherein the thickness of the sheet is smaller than the width of the gap, inserting the plurality of protruding connecting members through at least some of the plurality of openings into matching recesses of the plurality of recesses, applying ultrasonic energy to at least one of the first half frame and the second half frame to selectively heat at least portions of the connecting members and the recesses, and applying force to at least one of the first half frame and the second half frame to firmly weld the connecting members to the recesses.

In accordance with some embodiments of the methods of the present application, the step of applying ultrasonic energy includes applying a pulse of ultrasonic energy.

In accordance with some embodiments of the methods of the present application, the pulse of ultrasonic energy has a duration in the range of 0.1-2 seconds.

In accordance with some embodiments of the methods of the present application, the step of applying force begins prior to the step of applying ultrasonic energy.

In accordance with some embodiments of the methods of the present application, the step of applying force and the step of applying ultrasonic energy are performed simultaneously.

In accordance with some embodiments of the methods of the present application, the pulse of ultrasonic energy is terminated before the step of applying force begins, to avoid thermal damage to the sheet.

In accordance with some embodiments of the methods of the present application, the method includes the step of compressing the first half frame and the second half frame into a compressed state prior to performing the step of inserting.

In accordance with some embodiments of the methods of the present application, the first half frame and the second half frame include PEEK having a melting temperature of about 340° C. and the sheet includes polypropylene having a melting temperature of about 130° C.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings (in which like components are designated by like reference numbers) makes apparent to those skilled in the art how embodiments of the invention may be practiced.

In the drawings:

FIG. 3 is a schematic top view illustrating a "female" half frame of the pelvic implant of FIG. 2;

FIG. 4 is a schematic isometric view of the half frame of FIG. 3;

FIG. 5 is a cross sectional view of the half frame of FIG. 4 taken along the lines V-V;

DETAILED DESCRIPTION OF SPECIFIC EMBODIMENTS OF THE INVENTION

Figure 1:
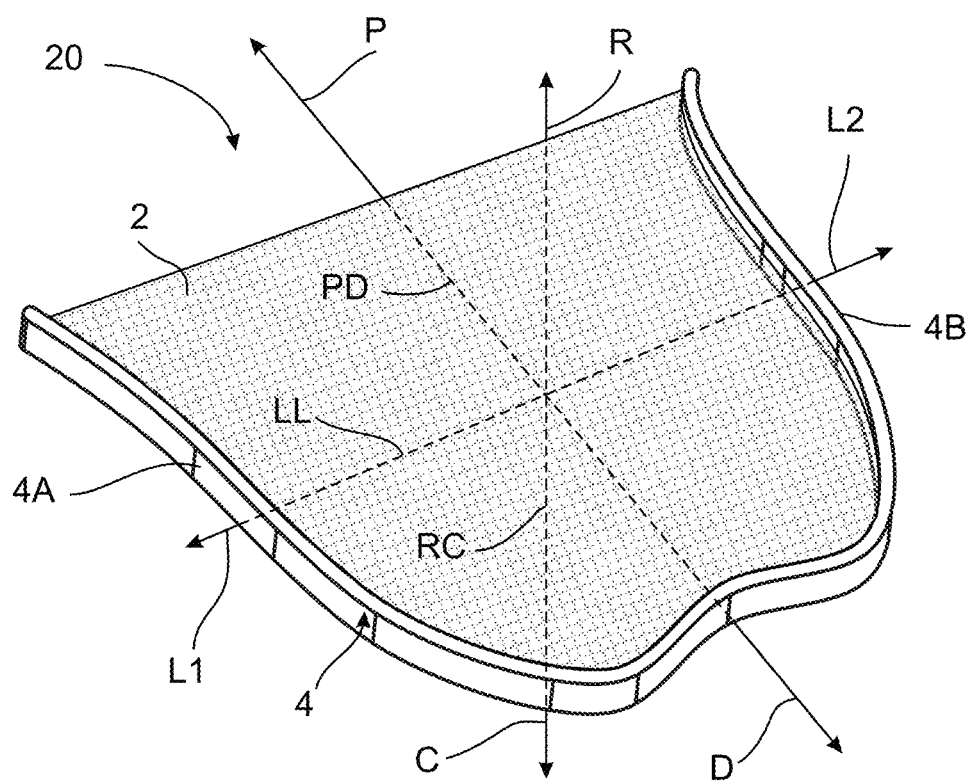
FIG. 1 is a schematic isometric view of a pelvic implant, in accordance with an embodiment of the implants of the present application.

Abbreviations:

The following abbreviations are used throughout the present application:

cm—centimeter mm-millimeter
PEEK—Polyether ether ketone
PP-Polypropylene
POP—pelvic organ prolapse
SUI—stress urinary incontinence The present invention, in some embodiments thereof, relates to implants for implantation in a body, methods of constructing and assembling implants and to methods for implanting of the implants.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. It is expected that during the life of a patent maturing from this application many new materials suitable for making implants will be developed and the scope of the terms "frame" and "sheet" are intended to include frames and sheets or meshes made from or including new materials a priori. As used herein the term "about" refers to ±10%. The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict. The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

For the purposes of the present application, the term "sheet" can be understood to include, but is not be limited to, a mesh, sheath, diaphragm, membrane, a divider and a multi-layered sheet. When the word "mesh" is used in relation to specific exemplary embodiments of such implants, it is noted that a sheet as defined hereinabove may also be used instead of a mesh in making the implant.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The present application discloses sheet implants for pelvic implantation for the treatment of hernia and pelvic organ prolapse (POP). Such implants typically use a soft and/or flexible and/or elastic sheet or mesh supported by a flexible elastic frame. As the frame has to have certain desired mechanical properties (such as, for example, sufficient strength, sufficient elasticity and flexibility) needed for supporting the mesh, this may necessitate the use of a material or materials for constructing the frame that have a melting point which may be much higher than the melting point of the mesh or sheet being supported by the frame. Assembly of the implant may require accommodating high and even harnessing tension throughout the length of the solid material without compromising the integrity of the mesh material (s) during the process of attaching the mesh to the frame and thereafter (including during the post-implantation time). Thus, if the assembly of the implant involves thermal bonding methods (such as, for example, ultrasonic welding and ironing) ensuring good bonding of frame parts holding the mesh without melting the delicate mesh held between the frame parts and without causing undesirable thermal damage to the mesh that may compromise the mesh's strength and postoperative performance (and/or other physical, mechanical or biological properties) which may result in implant's inferior performance or even failure after implantation. Thus, a large difference in the melting point of the material (s) included in the frame and mesh may thus result in certain challenges in assembling the implant by ultrasonic bonding or welding methods.

An advantage of some embodiments of the implants of the present application is a reduced tendency for irreversible changes in the mesh shape that may result in improved support for pelvic organs and which may reduce the probability of implant failure over time. The mesh (or sheet) sometimes sags after implantation, reducing the efficacy of support provided by the implant to a bladder or another pelvic organ disposed adjacent to the vaginal canal. Additionally, some embodiments of the implants of the present application may simplify and shorten the implantation duration, may reduce post-implantation mesh contraction and/or post-implantation mesh erosion and may reduce patient pain after implantation. The inventors of the present application have discovered that the pelvic implants disclosed herein perform significantly better as compared to prior art implants when the mesh or sheet thereof is held under tension after of the implantation.

The present application discloses novel implants as well as methods for constructing the implants.

Reference is now made to FIG. 1 which is a schematic isometric view of a pelvic implant, in accordance with an embodiment of the implants of the present application.

The implant 20 includes a sheet 2 and a frame 4. The sheet 2 may be attached to and held and supported by the frame 4. The sheet 2 may be a flexible member, comprised of a nylon mesh, a biological material (such as animal tissue, for example), or any other flexible biocompatible material. For example, the sheet 2 may be comprised of Prolene™, nylon, polypropylene (PP), Deklene™, polylactic acid, polyethylene glycol, polyester, synthetic biomaterials, allografts, autologous tissue, xenografts, heterografts, a collagen based sheet, or any combination of the above, or any other biocompatible material which is flexible and suitable for supporting a pelvic organ. It is noted that the above disclosed materials may be used in any of the sheets of any of the embodiments of the implants disclosed in the present application.

The frame 4 is comprised of or may include at least one solid, elastic supportive material, such as a polymer, a metal, or any other biocompatible material. For example, frame 4 may be comprised of PEEK, shape memory PEEK, polylactic acid, polyethylene glycol, synthetic biomaterials, titanium, stainless steel, shape-memory alloys, or any combination of the above, or any other biocompatible material which is flexible and suitable for providing support to sheet 2. In accordance with an embodiment of the implant, frame 4 may be comprised of a biodegradable material so that over time, frame 4 will degrade and be replaced by scar tissue which can then act as a support for the organs and/or the sheet 2. It is noted that any of the above disclosed materials or any combination of any of the above disclosed materials may be used in any of the frames of any of the embodiments of the implants disclosed in the present application.

It is noted that, while the sheet 2 as illustrated in FIG. 1 is, preferably, a mesh, other embodiments of the implants of the present application are contemplated in which the sheet 2 is implemented as a sheath, a diaphragm, a divider, a membrane, or any suitable type of multi-layered sheet. Additionally and/or alternatively, the frame 4 and/or the sheet 2, in any of the implementations disclosed in the present application, may be covered with or coated with any desired material or composition including any desired drug, and/or pharmaceutically active composition and/or a biologically active material. Examples of such materials and/or compositions may include, an anti inflammatory agent, an anti-bacterial agent, an anti viral agent, an antibiotic agent, a hormone, a biologically active protein, a biologically active polypeptide, a collagen (selected from one or more of any of the collagen types known in the art and any combination thereof), metallic ions, enzymes, enzyme precursors, biological promoters, a slow release matrix or a gel matrix containing any therapeutic agent(s), and/or pharmaceutical agent(s) and/or biologically active material(s) including but not limited to the above disclosed agents, materials and compositions or any combination of any of the above compositions, materials and agents.

The frame 4 may have two arms 4A and 4B. The material or materials included in frame 4 are such that the frame 4 is a flexible elastic frame. The frame 4 may have a relaxed configuration (relaxed state) and may also have a compressed configuration (compressed state) achieved by applying a force to the arms 4A and 4B such that the arms 4A and 4B elastically deform to reduce the distance between the arm 4A and the arm 4B and compress the frame 4. When the frame 4 is in the compressed state it may operate as a spring which may exert a force trying to restore the frame 4 to the relaxed configuration or state. In accordance with an embodiment of the implant, the sheet 2 is attached to the frame 4 while the frame 4 is in a compressed state. After the sheet 2 is attached to the frame 4, the arms 4A and 4B exert a force on the sheet 2 which results in the sheet 2 being held under tension. When the sheet 2 is attached to the frame 4, it prevents the frame 4 from returning to the relaxed state. Thus, after the attachment of the sheet 2 to the frame 4, the frame 4 is held in a compressed state by the sheet 2 and the sheet 2 is held under tension by the arms 4A and 4B. The tension under which the sheet 2 is held in the assembled implant 20 advantageously stabilizes the implant 20 and reduces post surgical sheet sagging and improves long term pelvic organs support efficacy as compared to implants with non-tensioned sheets.

Several methods are contemplated for attaching the sheet 2 to the frame 4 such that in the assembled implant the frame 4 is at least partially compressed to hold the sheet 2 under tension.

In accordance with one embodiment of the method for constructing an implant, the frame comprises two half frames which are assembled and attached to each other to hold the sheet under tension there between. The attaching of the half-frames to each other may be performed using any suitable method of attachment known in the art, such as, for example, thermal bonding, mechanical attachment methods or gluing, as is disclosed in detail hereinafter.

It is noted that in all the embodiments of the implants disclosed in the present application the opened end of the implant is referred to as the proximal end of the implant and the closed side of the implant is referred to as the distal end of the implant. In an example, in the implant 20 of FIG. 1, the arrow P points proximally and the arrow D points distally. In other of the drawing figures (for example, FIGS. 25 and 27 hereinafter) P represents the proximal side of the implant and D represents the distal side of the implant. In FIG. 1, the arrows L1, and L2 pointing laterally represent the lateral sides of the implant 20. The dashed line PD represents the proximo-distal axis of the implant 20. The dashed line LL represents a lateral axis of the implant. The axes PD and LL are orthogonal axes. The dashed line RC is orthogonal to the plane defined by the axes LL and PD and represents a rostro-caudal axis of the implant. It is pointed out that the term rostro-caudal axis is not related to the precise orientation of the implant within the body and is solely used as a convenient term referring to an axis orthogonal to the plane defined by the axes LL and PD.

The implant 20 is referred to as a flat implant solely to indicate that the arms 4A and 4B are not curved rostro-caudally with respect to the plane defined by the axes LL and PD (but may be contoured or curved laterally to fit better within the pelvic walls).

Figure 2:
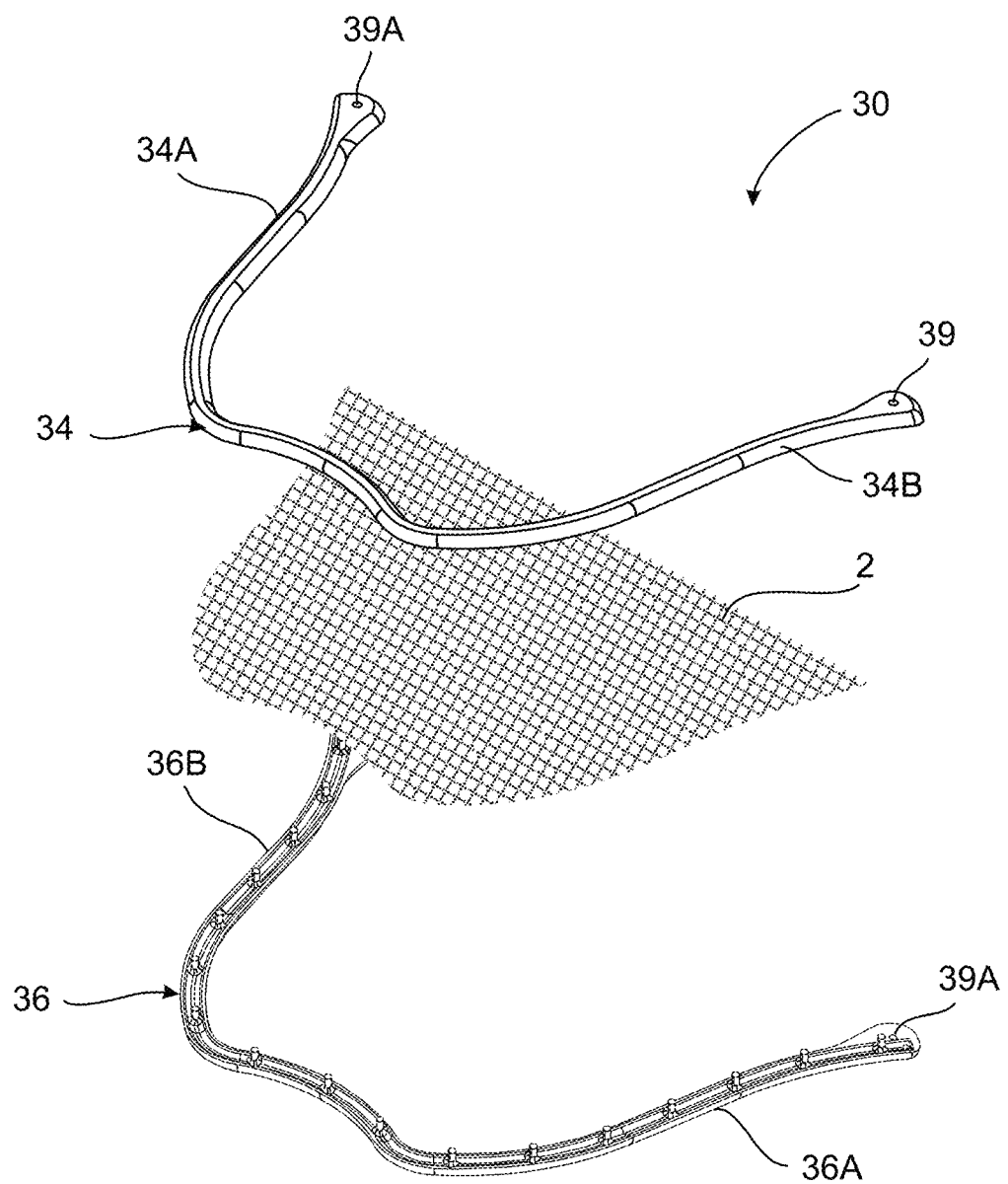
FIG. 2 is a schematic isometric exploded view of a pelvic implant including two half frames in accordance with an embodiment of the present application.
Figure 8:
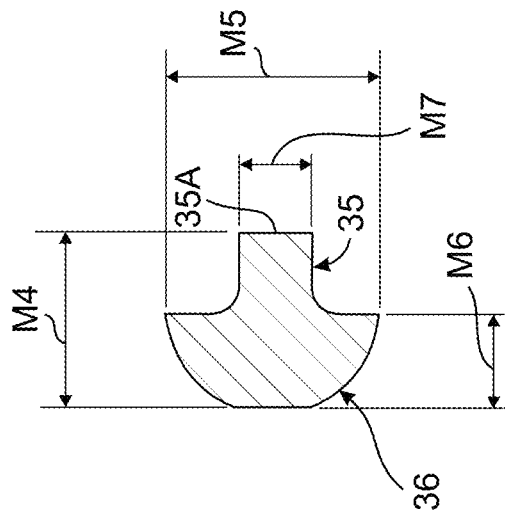
FIG. 8 is a cross sectional view of the half frame of FIG. 6 taken along the lines VIII-VIII.
Figure 7:
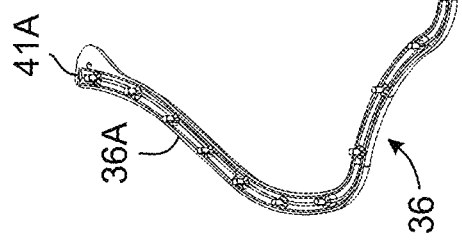
FIG. 7 is a schematic isometric view of the half frame of FIG. 6.
Figure 6:
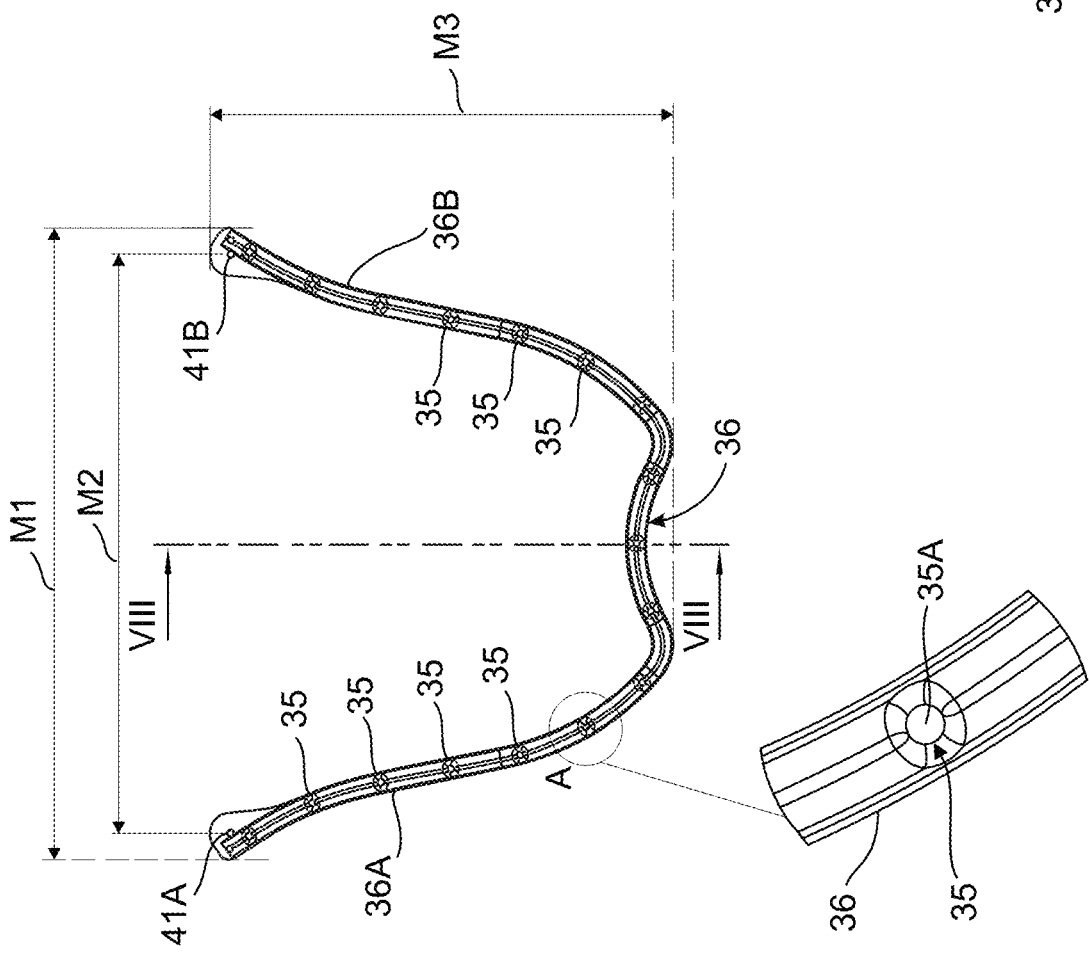
FIG. 6 is a schematic top view illustrating a "male" half frame of the pelvic implant of FIG. 2.

Reference is now made to FIGS. 2, 3-5 and 6-8. FIG. 2 is a schematic isometric exploded view of a pelvic implant including two half frames in accordance with an embodiment of the present application. FIG. 3 is a schematic top view illustrating a "female" half frame of the pelvic implant of FIG. 2. FIG. 4 is a schematic isometric view of the half frame of FIG. 3. FIG. 5 is a cross sectional view of the half frame of FIG. 4 taken along the lines V-V; FIG. 6 is a schematic top view illustrating a "male" half frame of the pelvic implant of FIG. 2. FIG. 7 is a schematic isometric view of the half frame of FIG. 6. FIG. 8 is a cross sectional view of the half frame of FIG. 6 taken along the lines VIII-VIII.

It is noted that the specific dimensions (in millimeter) of FIGS. 3, 5, 6 and 8 while given to demonstrate a practical example of the implant are no meant to be limiting and are given by way of example only. Any of the dimensions of the implants disclosed in the present application and in the drawing figures may be changed and made larger or smaller than the indicated dimensions. For example, it may be desirable to make the implants in several sizes having differing dimensions to accommodate for the natural variation in pelvic organs in different patients. Similarly, the dimensions, shapes, spacing and the number of the connecting members and the corresponding recesses in the half frames of some embodiments the implants of the present application may vary from those illustrated in the drawings in order to accommodate different types of meshes and/or sheets or due to mechanical design considerations.

Turning to FIG. 2, the implant 30 includes a sheet 2, a first half frame 34 and a second half frame 36. The first half frame 34 is a "female" half frame and the second half frame 36 is a "male" half frame. The sheet 2 is held and supported between the first half frame 34 and the second half frame 36 as disclosed in detail hereinafter. After assembly of the implant 30, the first half frame 34 and the second half frame 36 are firmly attached to each other and the sheet 2 is firmly held there between. The sheet 2 may be a flexible member, comprised of a mesh, or a contiguous sheet or a partially perforated sheet and may be made from any material or combination of materials as disclosed in detail hereinabove with respect to the sheet 2 of FIG. 1.

The first half frame 34 and the second half frame 36 may be comprised of a solid, supportive material or materials, such as a polymer, a metal, and/or any other biocompatible material(s) or biodegradable material(s) such as any of the material(s) disclosed in detail hereinabove with respect to the frame 4 of FIG. 1.

It is noted that while the sheet 2 as illustrated in FIG. 1 is, preferably, a mesh, other embodiments of the implant 30 are contemplated in which the sheet 2 is implemented as a sheath, a diaphragm, a divider or any suitable type of multi-layered sheet (with or without coating as disclosed in detail hereinabove with respect to the sheet 2 of FIG. 1). If the sheet 2 is not a mesh, the sheet 2 may have suitable perforations disposed along the perimeter of the sheet 2 to accommodate any connecting members formed in a "male" half frame (if used) as is disclosed in detail hereinafter.

The first half frame 34 has two arms 34A and 34B and the second half frame has to arms 36A and 36B. Turning to FIGS. 3 and 5, the first (female) half frame 34 has multiple recesses 32 formed therein. Each of the recesses 32 has a step-like annular contact region 38 formed therein. Turning to FIGS. 6 and 8, the second (male) half frame 36 has multiple protruding connecting members 35 formed therein. The position of each of the connecting members 35 along the half frame 36 matches the position of a recesses 32 formed in the first half frame 34, such that when the half frames 34 and 36 are aligned with each other, each of the connecting members 35 may be inserted into a corresponding recess 32 of the half frame 34. Each of the connecting members 35 may have a flat circular surface 35A at the end thereof. When the half frames 34 and 36 are aligned with each other and pressed together, each of the surfaces 35A of the connecting members 35 contacts the corresponding annular contact regions 38 of the corresponding recesses 32 of the half frame 34.

Typically, the dimensions M1-M9 of the half frames 34 and 36 may be within the following ranges: M1=70-120 mm, M2=60-100 mm, M3=40-100 mm, M4=1-5 mm, M5=2-6 mm, M6=0.5-3 mm, M7=0.5-4 mm, M8=0.5-4 mm, M9=0.4-3 mm, and (M9-M8)=0.1-2 mm. (M9-M8) is the width of the step 38 (of FIG. 5). However, some of the dimensions may be smaller than the lower values or larger than the upper values of the above indicated value ranges if necessary.

In accordance with one method for assembling an implant by using ultrasonic welding the following steps may be used. The second half frame 36 is placed on a flat surface (preferably, the surface of a stainless steel plate with the side having the protruding connecting members 35 facing upwards. A (preferably square, but other shapes of the mesh may also be used) piece of mesh larger in size than the size of the second half frame 36 is placed over the second half frame 36 such that the connecting members 35 pass through the holes in the mesh. After placement of the piece of mesh, the first half frame 34 is aligned with the second half frame 36 and placed over the mesh such that the connecting members 35 are inserted into the corresponding recesses 32 of the first half frame such that each surface 35A is in contact with the step-like annular contact region 38 of the corresponding recess 32 into which the connecting member is inserted. A plate of an ultrasonic welder is lowered and put into firm contact with the upper surface of the first half frame 34. At this stage the mesh is held between the second half frame 36 and the first half frame 34. Ultrasonic energy is them applied by the ultrasonic welder to ultrasonically weld the first half frame 34 to the second as disclosed in detail hereinafter. After the welding is completed, the excess parts of the mesh protruding from the periphery of the assembled implant are trimmed (for example, by a suitable cutting laser) or cut by any other suitable trimming method known in the art to form the form the final assembled implant.

Due to the mechanical and other requirements of the implant, in accordance with one non-limiting embodiment of the implant, the first and second half frames 34 and 36 of the implant may be made from PEEK which has a melting point of about 340° C. The mesh may be made from polypropylene (PP) which has a melting point of about 130° C. Therefore, assembly of the frame from the first half frame 34, the second half frame 36 and the mesh by using ultrasonic welding as disclosed hereinabove is non-trivial and requires very careful tuning of the ultrasound application parameters in order to achieve a firm attachment of the first and second half frames 34 and 36 to each other without causing thermal damage or melting of the polypropylene mesh due to thermal conduction of heat from the half frames 34 and 36 to the mesh being held between them during welding.

If the opposing surfaces of the half frames are in close contact with the sheet or the mesh and the half frames are pressed firmly to the surface of the sheet, the ultrasonic vibrations applied to the frame during the welding cause significant friction between the surfaces of the half frames contacting the sheet resulting in too much heat being produced at the contacting vibrating surfaces of the mesh and half frames during the welding process. This heat will cause the mesh to become damaged by fully or partially melting at the area where the mesh is held in firm contact between the half frames 34 and 36 resulting in a completely or partially damaged or weakened mesh which may result in inferior mechanical performance of the mesh in supporting pelvic organs or even in complete implant failure during or after implantation. On the other hand, if too little heat is produced during welding, the result may be either a failure to attach the first half frame 34 to the second half frame 36 or an inferior or insufficient mechanical properties of the attachment points which may result in undesirable implant performance due to separation of the two half frames 34 and 36 from the mesh under mechanical stresses to which the implant may be subjected after implantation. This problem may be exacerbated in implants in which the sheet or mesh is held under tension as will be described hereinafter with respect to another embodiment of the implants of the present application. In such embodiments, the tension under which the mesh is held may result in even larger damages to the mesh resulting from excessive mesh heating while the mesh is constantly subjected to stretching forces applied to the mesh by the frame.

The inventors of the implants of the present application have discovered that it is possible to efficiently and satisfactorily ultrasonically weld (or thermally bond) the first half frame and the second half frame of the implants described in the present application without thermally damaging the mesh used in the implants by avoiding close contact between the sheet (or mesh) and the frame halves during the time of application of the ultrasonic welding pulse to the implant. This method may be implemented by modifying the structure of the half frames to provide a space or gap separating between the opposing surfaces of the half frames during the application of the ultrasound to the. This space or gap or separation results in the opposing surfaces of the half frame not being in close and firm contact which greatly reduces the amount of friction between the surfaces of the sheet and the opposing surfaces of the frame halves between which the sheet is disposed.

Figure 9:
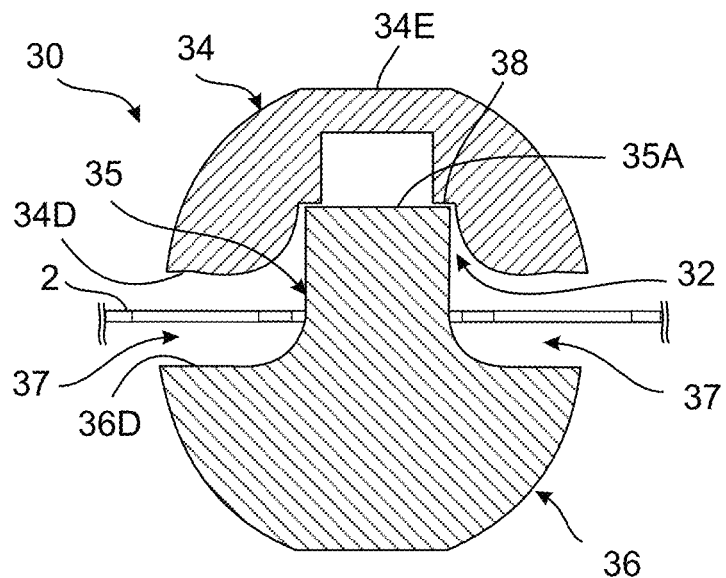
FIG. 9 is a schematic cross sectional view illustrating part of an implant before ultrasonic welding.
Figure 10:
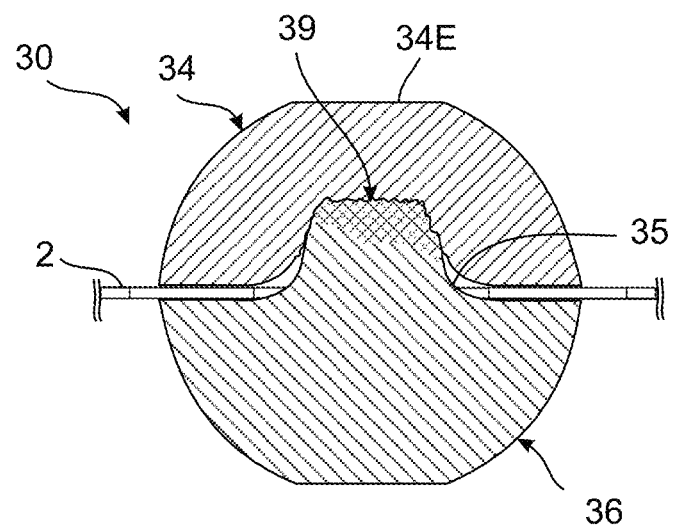
FIG. 10 is a schematic cross section view illustrating the same part of the implant of FIG. 9 after the ultrasonic welding.

Reference is now made to FIGS. 9 and 10. FIG. 9 is a schematic cross sectional view illustrating part of an implant before ultrasonic welding and FIG. 10 is a schematic cross section view illustrating the same part of the implant of FIG. 9 after the ultrasonic welding.

Turning to FIG. 9 the connecting member 35 of the half frame 36 passes through a hole of the mesh 2 and the flat surface 35A of the connecting member 35 may contact the step 38 of the first half frame 34. The recess 32 has a step 38 formed therein. When a connecting member 35 is inserted into a recess 32, the flat surface 35A of the connecting member 35 contacts part of the surface of the step 38 and is stopped from moving further into the recess 32 as the surface 35A contacts the surface of the step 38 The position of the step 38 within the recesses 32 and the length of the connecting members are such that when the sheet 2 is disposed between the frames 34 and 36 by inserting the connecting members 35 through holes formed in the sheet 2 (or in any mesh being used) and the half 34 and the frame half 36 are firmly pushed together (For example by a vibrating plate of the ultrasonic welder being used), the surfaces 35A of the connecting members 35 engage in firm contact with the steps 38 of the recesses 32 resulting in a gap 37 being left between the surfaces 34A and 36A, of the half frames 34 and 36.

The dimensions of the gap 37 are such that the sheet 2 is not firmly pressed between the surfaces 34A and 36B, while the surface (s) 35A are firmly engaged by the surface of the step 38 and in firm contact therewith. When a short ultrasonic pulse is applied to the surface 34E, the regions of contact of the step 38 and the surfaces 35A heat and are softened (or may even melt or partially melt) because of the friction resulting from their vibrations against each other, resulting in a firm connecting between the half frames 34 and 36. By adjusting the parameters of the ultrasonic pulse delivered to the implant during welding (including, among others, ultrasonic pulse duration, ultrasound frequency, and ultrasound intensity), the amount of heat locally produced at the contact regions between the steps 38 and the surfaces 35A may be controlled such that the heat is sufficient to melt or partially melt the end of the connecting member 35 resulting in an adequate weld strength. However since during the application of the ultrasound pulse almost no heat is produced at the surfaces of the sheet 2 (due to the gap 37 preventing any firm contact between the surfaces of the sheet 2 and the surfaces 36D and 34D as explained above), this prevents any thermal damage to the sheet 2. Furthermore, because of the structure of the recesses 32 and the connecting members 35, any debris formed during the welding is kept away from the sheet 2 further protecting the sheet 2 from thermal damage by any such hot welding debris. It is noted that due to the short ultrasound pulse duration, at the step of the application of mechanical force by the ultrasonic welder upper plate to the surface 36E of the first half frame 34 (which results in bringing the surfaces 34A and 36A in firm contact with the sheet 2), the ultrasound pulse has already ended so there is no possibility for direct local heat generation at the surfaces of the sheet 2.

It is noted that the ultrasonic welding method as disclosed in detail hereinabove with respect to FIGS. 9 and 10 has several advantages, including the fact that the frame remains relatively smooth as the connecting members are "hidden" inside the assembled frame and do not protrude on the outside surface of the assembled frame. However, in accordance with another embodiment of the present implants, the two half frames may also be attached to each other by a "nailing" method in which the male half frame includes connecting member which are sufficiently long to pass through thickness of the female half frame and in which the female half frame includes open passages extending there through.

Figure 11:
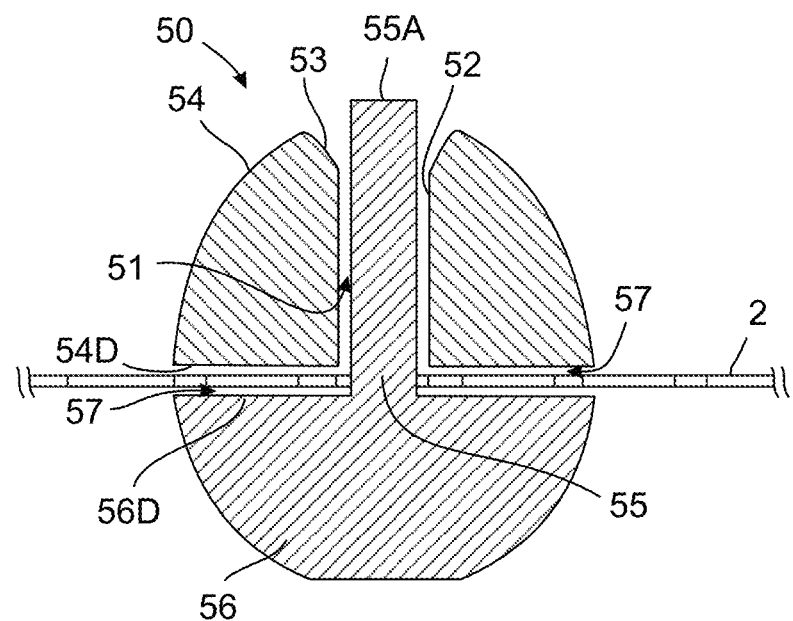
FIG. 11 is a schematic cross sectional diagram illustrating part of an implant having two half frames in accordance with another embodiment of the implants of the present application shown during a first stage of assembly of the implant.
Figure 12:
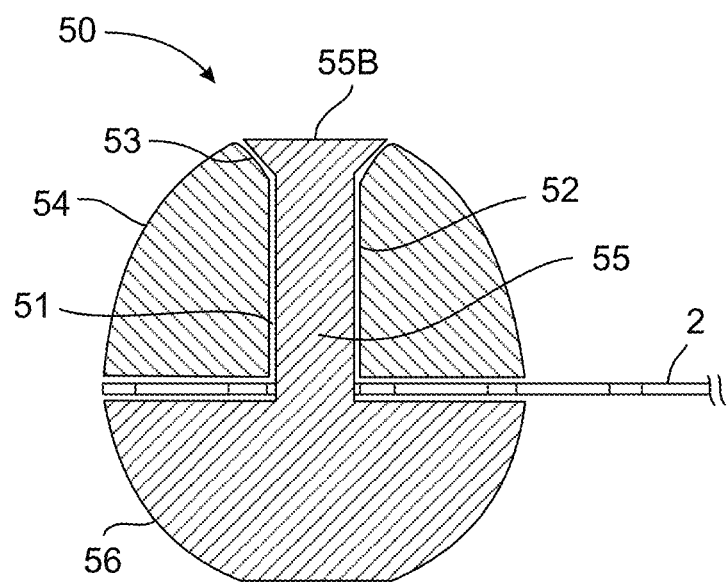
FIG. 12 is a schematic cross sectional diagram illustrating part of an implant of FIG. 11 shown during another stage of assembly of the implant.

Reference is now made to FIGS. 11-12. FIG. 11 is a schematic cross sectional diagram illustrating part of an implant having two half frames in accordance with another embodiment of the implants of the present application shown during a first stage of assembly of the implant. FIG. 12 is a schematic cross sectional diagram illustrating part of an implant of FIG. 11 shown during another stage of assembly of the implant.

The implant 50 includes a sheet 2 as disclosed hereinabove in detail, a first half frame 54 and a second half frame 56. The first half frame 54 is similar in shape and material composition to the first half frame 34 of FIG. 4, except that instead of the recesses 32 of the first half frame 34, the first half frame 54 may include a plurality of open passages 51 therein. Each open passage 51 may have a cylindrical hollow portion 52 opening on one side of the first half frame 54 and a second frustoconical portion 53 opening on a second side of the half frame 54. The second half frame 56 may be similar in shape and material composition to the second half frame 36 of FIG. 8, except that instead of the connecting members 35 of the second half frame 36, the first half frame 54 includes a plurality of cylindrical connecting members 55 therein. The diameter of the cylindrical connecting members 55 may be slightly smaller than the diameter of the cylindrical hollow portion 52 of the open passage 51 such that the connecting member 55 may be easily inserted into the hollow passage 51. The connecting members 55 are longer than the total length of the open passage 51, such that when a connecting member 55 is inserted into the open passage 51 the end 55A of the connecting member 55 extends beyond the wider open end of the frustoconical portion 53 as may be seen in FIG. 11. The implant 56 may be assembled by, preferably (but not obligatorily) thermal bonding using ironing or by any other suitable thermal bonding method (such as, for example, ultrasonic welding) or a mechanical assembling method as is disclosed in detail hereinafter.

If ultrasonic welding is used to assemble the implant 50, the second half frame 56 may be placed on a flat plate ("Jig") of the welder (not shown in FIG. 11, but see FIGS. 18-21, hereinafter), the mesh 2 may be aligned and placed on top of the second half frame 56 such that each of the plurality of connecting members 55 passes through a hole or perforation of the mesh 2 (as seen in FIG. 11). The first half frame 54 may then be aligned with the second half frame 56 and lowered towards the mesh 2 until the plurality of connecting members 55 protruding from the mesh 2 enter into the corresponding plurality of open passages 51 and protrude from the wider open end of the frustoconical portions 53 as is shown in FIG. 11. A second plate of the ultrasonic welder (not shown) may then be lowered until it contacts the ends 55A of the connecting members 55. Ultrasonic energy (preferably in a short pulse) may then be briefly applied by the welder to heat the protruding ends 55A of the connecting members 55 until they soften and/or melt and then a mechanical force is applied by lowering the second (upper) welder plate to reshape and widen the ends 55A of the connecting members 55. Turning to FIG. 12, the mesh 2, the first half frame 54 and the second half frame 56 are illustrated (in a cross sectional view) after assembly. The end 55B of the connecting member 55 is shown as reshaped after ultrasonic welding the end 55B is no longer cylindrical in shape but has expanded laterally to fill in the frustoconical portion 53 (and may possibly also have fused or partially fused with the walls of the frustoconical portion 53 (it is noted that fusing is not shown in FIG. 12 for the sake of clarity of illustration). After welding, the laterally expanded parts 55B of the connecting members 55 firmly hold the first half frame 54 the second half frame 56 and the mesh 2 together since the expanded end 55B of the welded connecting members 55 cannot pass through the cylindrical portion 52. It is noted that in FIG. 12, the mesh 2 is illustrated after it has been trimmed (by laser cutting or by any other suitable method known in the art) as disclosed in detail hereinabove.

It is noted that in embodiments of the implant using the open passages 51 and corresponding connecting members 55, ultrasonic welding (or any other suitable thermal bonding method such as ironing) may be effectively applied for assembling the implant without causing damage to the mesh 2 because due to the increased length of the connecting members 55 (as compared to the length of the connecting members 35 of FIG. 8), the heated region at the ends 55A of the connecting members 55 is further away from the mesh 2 and due to the low thermal conductivity of the PEEK or other material of the frame very little heat may reach the sheet 2. Additionally, because during the application of ultrasound to the ends 55A, no force is applied to the half frame 54 at all, because the welding plate engages only with the surfaces 55A at this stage and does not engage any part of the half frame 54, resulting in a gap 57 existing between the surface 34D of the half frame 54 and the surface 56D of the half frame 56. Consequently, the sheet 2 is not in firm contact with the surfaces 56D and 54D and there is no friction between the surfaces of the sheet 2 and the surfaces 54D and 56D and therefore, no heat is being locally directly generated at or near the sheet 2.

In accordance with yet another embodiment of the implant assembly methods of the present application, a thermal bonding such as ironing may be used for assembling the implants. For example, turning to FIG. 11, the implant 50 may be assembled by placing the second half frame 56 on a flat surface (such as, for example a stainless steel plate or Jig as disclosed hereinabove, placing the mesh 2 on the second half frame such that the connecting members are inserted through the perforation of the mesh 2 and then aligning the first half frame 54 with the second half frame 36 and lowering the first half frame towards the mesh 2 such that all the connecting members 35 are disposed within the corresponding open passages 51 and the ends 35A of the connecting member 35 are protruding through the wider ends of the corresponding frustoconical portions 53. A hot flat ironing plate (not shown for the sake of clarity of illustration) may then be contacted with the ends 35A and a downward force is applied to the ironing plate by moving the ironing plate downward (towards the direction of the mesh 2) to cause heating and or melting or partial melting and to widen the heated and softened ends 35A such that they fill the frustoconical portions 53. The movement of the ironing plate may be (optionally) stopped before the lower surface of the ironing contacts touches the uppermost part of the first half frame 54 and the hot ironing plate may then be lifted off the assembled implant. A step of trimming the mesh laterally protruding from the sides of the implant may be performed by laser cutting or any other trimming method known in the art as disclosed hereinabove.

The ironing method described hereinabove results in the same attaching of the half frames 54 and 56 to each other with the mesh 2 firmly held therebetween. The sheet 2 is kept undamaged due to the length of the connecting member 55 assisting in heat dissipation by thermal conduction into the second half frame 56, such that the temperature of the surfaces of the half frame 56 which are in contact with the mesh 2 do not reach the melting temperature of the mesh 2 preventing any significant thermal damage to the mesh 2. If ironing by a hot plate and application of force is being used to soften and/or expand and/or widen the ends 55A of the connecting members 55 for assembly of the implant, the sheet 2 is even better protected from any thermal damage because there is no ultrasound application at all being used in ironing eliminating any possibility at all of ultrasonic vibrations from reaching any part of the sheet 2. Thus, ironing may actually be a preferred (though not obligatory) method of thermally bonding half frames of the type used in the implant 50 (of FIGS. 11-12). The parameters of the ironing (such as, for example, the ironing plate temperature, the duration of ironing plate contact with the implant, the duration and magnitude of force application) may be adjusted such that the first and the second half frames 54 and 56, respectively, may become strongly and firmly attached to each other without causing thermal damage to the mesh 2. Furthermore, irrespective of whether ultrasonic welding or ironing is being used to assemble the implant 50, the positions of the thermally treated ends 55A of the connecting members connecting member away from the sheet 2 reduces the possibility that any hot debris formed during ultrasonic welding or ironing may reach the sheet 2 further reducing the possibility of the sheet 2 being thermally damaged.

It is noted that the ironing parameters may depend, inter alia, on the size and dimensions of the implant being assembled, its thermal mass, thermal conductivity and other thermal characteristics of the material(s) from which the frame and mesh (or sheet) are formed.

It is noted that the "nailing" method disclosed hereinabove is not limited to the use of thermal methods. For example, in accordance with another method of the methods of implant assembly of the present application, mechanical methods may be used for attaching the half frames 54 and 56 to each other. Returning to FIG. 11, after the first half frame 54, the second half frame 56 and the mesh 2 have been arranged as illustrated in FIG. 11 a suitable mechanical tool (such as, for example a suitable punch or tool) may be used to mechanically broaden the ends 55A of the connecting members 55 to fasten the first half frame 54 to the second half frame 56 (with the mesh 2 firmly held between the half frames 54 and 56). Such a punch (not shown) may be any type of punch suitable for broadening the end 55A, such as, for example, a punch having a conical end or a punch having a tapering end. When using a mechanical method for assembling the two half frames 54 and 56 and the mesh 2 together instead of using thermal methods (such as, inter alia, ultrasonic welding and ironing) the problem of damaging the mesh 2 is resolved since excessive heating that may thermally damage the mesh 2 does not occur.

Figure 13:
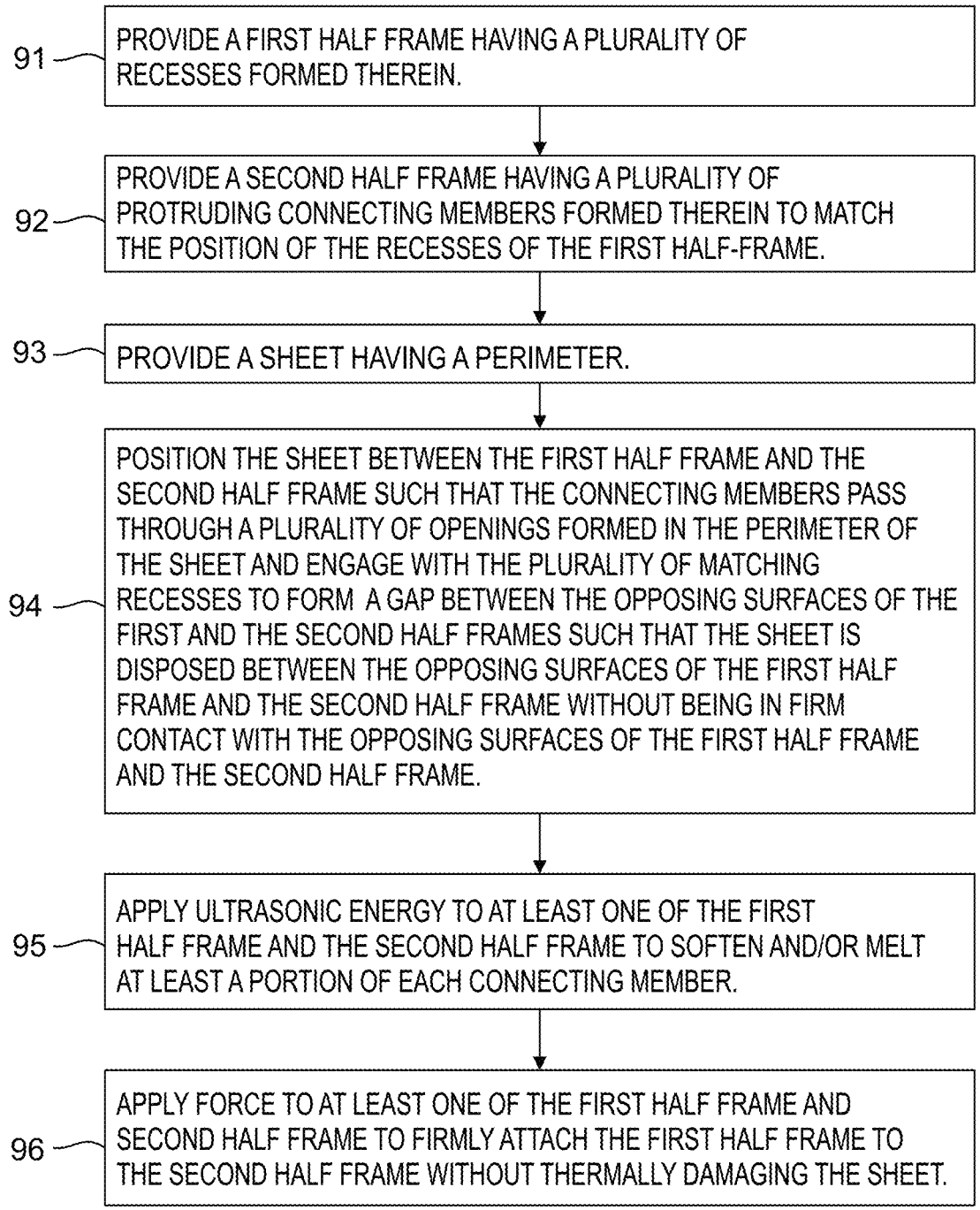
FIG. 13 is a schematic flow chart illustrating the steps of a method for assembling an implant by using ultrasonic welding, in accordance with an embodiment of the methods for implant assembly of the present application.

Reference is now made to FIG. 13 which is a schematic flow chart, illustrating the steps of a method for assembling an implant by using ultrasonic welding, in accordance with an embodiment of the methods for implant assembly of the present application.

The method includes providing a first half frame (such as the exemplary half frame 34 of FIGS. 3, 9 and 10) having a plurality of recesses (such as the exemplary recesses 32 of FIGS. 3 and 5) formed therein (step 91). The method also includes providing a second half frame (such as the exemplary half frame 36 of FIGS. 6, 9 and 10) having a plurality of protruding connecting members (such as the exemplary connecting members of FIGS. 6, 8, 9 and 10) formed therein to match the positions of the recesses of the first half-frame (step 92). The method also includes providing a sheet (such as the exemplary sheet 2 of FIGS. 2, 9 and 10). The sheet has a perimeter (step 93). The method also includes positioning the sheet between the first half frame and the second half frame such that the connecting members pass through a plurality of openings formed in the perimeter of the sheet and engage with the plurality of matching recesses to form a gap (such as for example the gap 37 of FIG. 9) between the opposing surfaces (such as the exemplary opposing surfaces 34D and 36D of FIG. 9) of the first and the second half frames, such that the sheet is disposed between the opposing surfaces of the first half frame and the second half frame without being in firm contact with the opposing surfaces of the first half frame and the second half frame (step 94). The method also includes applying ultrasonic energy (in the form of ultrasonic vibrations) to at least one of the first half frame and the second half frame to soften and/or melt at least a portion of each connecting member (step 95). The method also includes applying force to at least one of the first half frame and second half frame to firmly attach the first half frame to the second half frame without thermally damaging the sheet (step 96).

The method is suitable for attaching a sheet (such as, but not limited to, the sheet 2 of FIG. 2) having a first melting temperature to a supporting frame (such as, but not limited to, the frame 34 of FIG. 2) having a second melting point when the second melting point is substantially higher than the first melting temperature. In an exemplary embodiment the half frames 34 and 36 may be made from PEEK having a melting point of about 340° C. and the sheet 2 may be a mesh formed from polypropylene having a melting temperature of about 130° C., necessitating the use of the above method to avoid thermal damage to the sheet 2 during ultrasonic welding of the implant.

It is noted that the method disclosed hereinabove and illustrated in detail in FIGS. 18-21 hereinafter, may be used for assembling any type of implant requiring attachment of two half frames and a sheet or a mesh held between the two half frames by forming in the half frames corresponding connecting members and matching recesses where the contact region between the connecting members and the recesses or open passages may be limited to control the amount of heat reaching the sheet or mesh by thermal conduction through the heated (by ultrasonic welding or by ironing/nailing as disclosed hereinabove).

Figure 14:
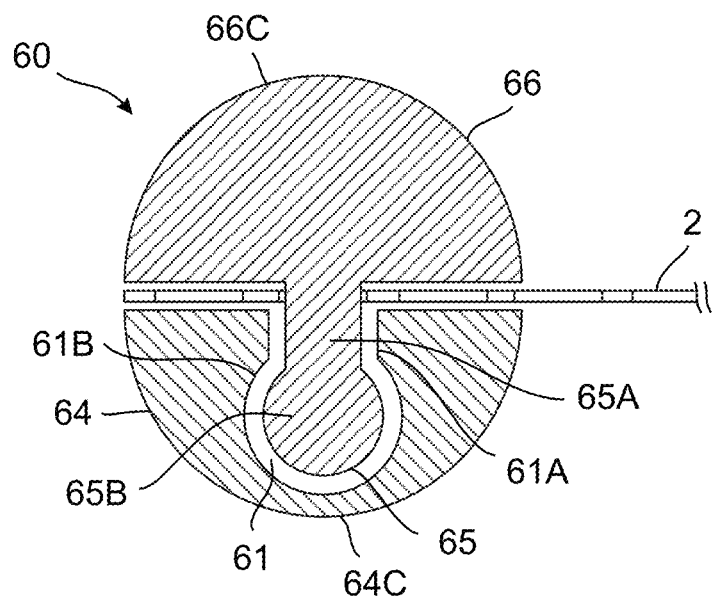
FIG. 14 is a schematic cross sectional view illustrating part of an implant configured for being mechanically assembled and using hidden connecting members, in accordance with another embodiment of the implants of the present application.
Figure 15:
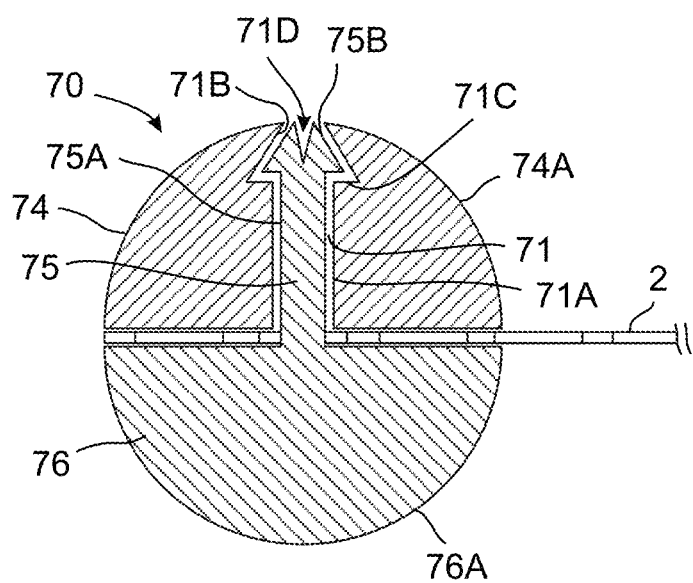
FIG. 15 is a schematic cross sectional view illustrating part of an implant configured for being mechanically assembled and using through passing connecting members, in accordance with another embodiment of the implants of the present application.

It is noted that in accordance with yet other embodiments of methods for implant assembly, the implants of the present application may be configured for enabling mechanical assembling thereof. Reference is now made to FIGS. 14 and 15. FIG. 14 is a schematic cross sectional view illustrating part of an implant configured for being mechanically assembled and using hidden connecting members, in accordance with another embodiment of the implants of the present application. FIG. 15 is a schematic cross sectional view illustrating part of an implant configured for being mechanically assembled and using through passing connecting members, in accordance with another embodiment of the implants of the present application.

Turning to FIG. 14, the implant 60 includes a first (female) half frame 64, a second (male) half frame 66 and a mesh 2. The first half frame 64 is similar in shape and material composition to the first half frame 34 of FIG. 4, except that instead of the recesses 32 of the first half frame 34, the first half frame 64 includes a plurality of recesses 61 therein. Each of the recesses 61 may have a cylindrical hollow recess portion 61A opening on one side of the first half frame 64 and a second spherical hollow recess portion 61B extending from the cylindrical recess portion 61A. The second half frame 66 is similar in shape and material composition to the second half frame 36 of FIG. 8, except that instead of the connecting members 35 of the second half frame 36, the second half frame 66 includes a plurality of "snap-in" connecting members 65 therein. Each of the connecting members 65 includes a cylindrical portion 65A and a spherical portion 65B extending from the cylindrical portion 65A. The diameter of the cylindrical portion 65A is slightly smaller than the diameter of the cylindrical hollow portion 61A of the recess 61 and the diameter of the spherical portion 65B of the connecting member 65 is slightly smaller than the diameter of the spherical hollow portion 61B of the recess 61, such that the connecting member 65 may be accommodated within the hollow passage 61. As the material from which the half frame 66 and the half frame 64 are made off is elastic, when the spherical portion 65B is placed in contact with and forcefully pushed into the opening of the cylindrical hollow portion 61A, the spherical portion 65B may be "snapped" into the spherical portion 61B.

When the implant 60 is assembled, the mesh 2 may be placed on the second half frame 66 such that each of the connecting members 65 is inserted into an opening in the mesh 2. The first half frame may then be aligned and placed on top of the mesh 2, such that each of spherical portions 65B of the connecting members 65 is put in contact with the opening of the cylindrical portion 61A of the corresponding recess 61. An adequate force may then be applied to the half frame 64 until all the connecting members 65 snap into the corresponding recesses 61 to firmly attach the first half frame to the second half frame with the mesh 2 firmly harnessed and held between the half frames 64 and 66. It is noted that after assembly of the implant 60, the connecting members 65 are completely hidden within the half frame 64 resulting in a relatively smooth contour of the outer surface 64C of the half frame 64 and of the outer surface 66C of the half frame 66.

The construction and operation of such "snap-in" male/female connectors is well known in the art and is therefore is not discussed in detail hereinafter. It is noted that the implants of the present application are not limited to using the particular exemplary shape and type of the recesses 61 and of the connecting members 65 of the implant 60 the recess, rather, it is contemplated that the implants of the present application may use any type and shape of snap-in recesses and connecting members known in the art.

Turning to FIG. 15, the implant 70 is adapted to use a different type of mechanical assembly. The implant 70 includes a first (female) half frame 74, a second (male) half frame 76 and the mesh 2. The first half frame 74 is similar in shape and material composition to the first half frame 54 of FIG. 11, except that instead of the recesses 52 of the first half frame 54 (of FIG. 11), the first half frame 74 includes a plurality of open passages 71 therein. Each open passage 71 may have a cylindrical hollow portion 71A opening on one side of the first half frame 74 and a second frustoconical hollow portion 71B opening on a second side of the half frame 74. The hollow frustoconical portion has a flat annular surface 71C at the side thereof connected with the hollow cylindrical portion 71A and has an opening 71D at the side thereof opening on the outer surface 74A of the half frame74.

The second half frame 76 is similar in general shape and material composition to the second half frame 56 of FIG. 11, except that instead of the connecting members 55 of the second half frame 56 (of FIG. 11), the second half frame 76 includes a plurality of split pin connecting members 75 therein. Each of the connecting members 75 has a cylindrical portion 75A having a cross-sectional diameter that is slightly smaller than the cross-sectional diameter of the cylindrical portion 71A of the recess 71. Each of the connecting members 75 has a split head portion 75B suitable for insertion into the hollow cylindrical portion 71A of the recess 71. Preferably (but not obligatorily), after the assembly of the implant 70, the end of the split head 75B is flush with the opening 71B and does not protrude from the outer surface 74A of the first half frame 74 (as seen in FIG. 15). However, in accordance with other embodiments of the implant, the end of the split head 75B may either protrude through the surface 74A or may be shorter than illustrated in FIG. 15 such that it may end lower than the opening 71D and is also not protruding through the opening 71D and beyond the surface 74A.

When the implant 70 is being assembled, the mesh 2 may be aligned and placed upon the second half frame 76 such that each of the connecting members 75 passes through on of the openings of the mesh 2. The first half frame 76 may then be aligned and placed on top of the mesh 2 such that each of the split heads 75B is placed opposite the corresponding opening of the matching open passage 71. The first half frame 74 may then be forcefully pushed towards the first half frame 76 such that the split heads 75B are forced to reduce their cross sectional perimeter and pass through the corresponding hollow cylindrical portions of the second half frame 74 until they reach the frustoconical portions 71B where they may expand to firmly attach the first half frame 74 and the second half frame 76 such that the mesh 2 is firmly held and harnessed between the two half frames 74 and 76.

It is further noted that the frustoconical shape of the hollow frustoconical portion 71B is not obligatory and that the second portion of the open passages 71 may have any suitable shape for holding the split head 75B (such as, for example, a cylindrical hollow portion having a cross-sectional diameter larger than the cross sectional diameter of the hollow cylindrical portion 71A). The frustoconical portions 71B may be modified into any shape or structure suitable to receiving therein the split heads 75B for firmly connecting the two half frames 74 and 76.

While the embodiments of the implants disclosed hereinabove disclose excellent implants constructed from two complementary half frames and several methods for harnessing and holding a sheet or mesh between the half frames, the sheet or mesh supported by the frame may typically be made of a synthetic soft material that may change its shape over time due to dynamic forces applied thereto by the surrounding organs. The frame used in such implants provides mechanical support for the mesh reducing the probability for irreversible changes in the mesh shape that may result in implant failure over time. However, the mesh or sheet sometimes sags after implantation, reducing the efficacy of support provided by the implant to a bladder or another pelvic organ disposed adjacent to the vaginal canal. In order to solve such post-implantation mesh sagging and/or post-implantation mesh folding problems the inventors have invented a novel type of implants in which the sheet or mesh is harnessed in a frame and is held under tension after the implants assembly. In the novel implants of the present application, the sheet or mesh of the implants is held under tension also after the implantation of the implant in the pelvis and significantly improves the post-implantation implant's performance as is disclosed in detail hereinafter.

In accordance with an embodiment of the implants of the present application, may be similar in structure to any of the implants 20, 30, 40, 50, 60 and 70 disclosed hereinabove. However, during assembly of the implants, the elastic frame or the parts of the frame (when a frame made from two half frames as disclosed in detail hereinabove) are compressed until they are in a compressed state (or compressed configuration). The sheet or mesh may then be assembled between the half frames while the half frames (or, alternatively, the frame if a monolithic frame is used as will be disclosed in detail hereinafter) are both in a compressed state. After assembly of the implant (by any assembly method disclosed hereinabove, including, inter alia, any of the mechanical assembly methods and thermal bonding methods), the compressed elastic frame exerts a restoring force trying to return into its relaxed state (relaxed configuration). However, since the sheet or mesh is now attached to the frame, the sheet or mesh of the implant is tensioned by the restoring forces exerted thereon by the frame and does not allow the frame to return to its fully relaxed state or relaxed configuration. In such implants, the sheet (or mesh) and the frame of the implant are under tension.

Figure 16:
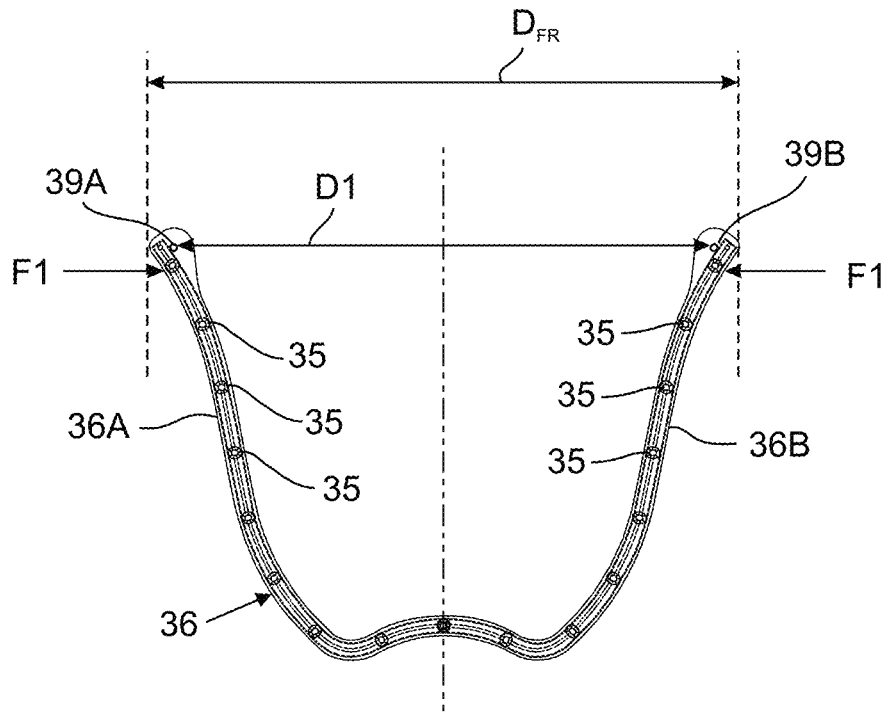
FIGS. 16-17 are schematic top view diagrams illustrating two different states of the elastic second half frame 36 of FIG. 6.
Figure 17:
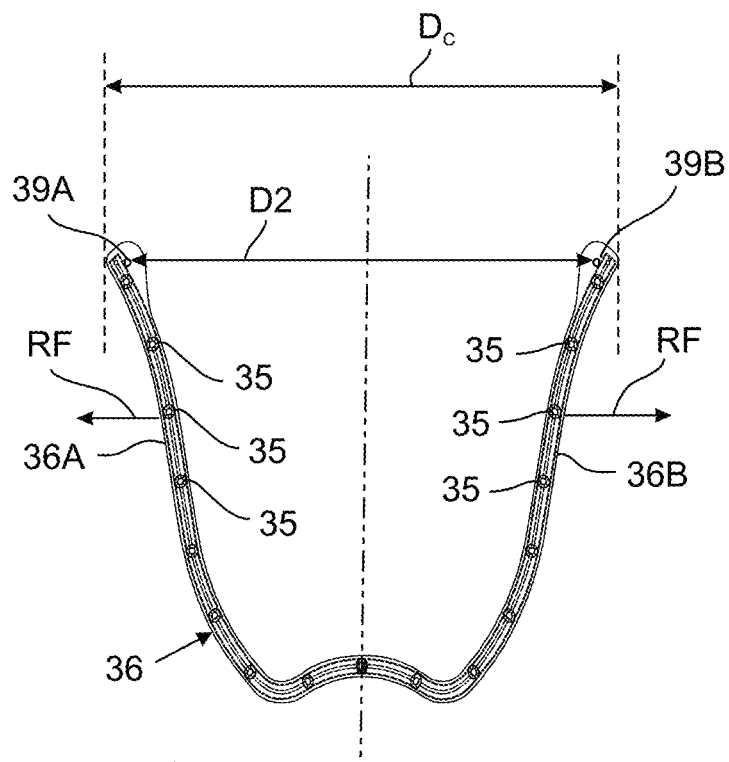

Reference is now made to FIGS. 16 and 17 which are schematic top view diagrams illustrating two different states of the elastic second half frame 36 of FIG. 6. Turning to FIG. 16, the second half frame 36 is identical to the second half frame 36 of FIGS. 6-8. The second half frame 36 is shown in a fully relaxed state or configuration. In the fully relaxed state illustrated in FIG. 16, the distance between the proximal ends of the arms 36A and 36B (measured as the distance between the attachment passages 39A and 39B) is D1. If a compressing force is applied to the arms 36A and 36B in the directions represented by the two arrows F1, the elastic second half frame 36 will bend and become compressed resulting in the two arms 36A and 36B moving one towards the other and the distance between them shortens. Turning to FIG. 17, the second half frame 36 is illustrated in a compressed state (compressed configuration) resulting from the application of force to the half frame 36. The distance between the two ends of the arms 36A and 36B is now D2 (wherein D2<D1). As long as the compressing force is applied to the half frame 36 it remains in the compressed state. Due to the elasticity of the half frame 36, it will act as a spring and if the compressing force is not applied any more to the half frame 36, a restoring force RF (represented schematically by the two arrows labeled RF), will return the arms 36A and 36 to their former position before the half frame 36 was compressed. It is noted that the distance D2 will depend on the magnitude of the compressing force F1 applied to the half frame 36. Within a certain range of forces the distance D2 will linearly depend on the magnitude of the compressing force F1 (this range of force magnitudes is termed the liner range and may depend inter alia on the properties of the material(s) forming the half frame 36. This restoring force RF may be used to hold a sheet or mesh (such as, for example, the mesh 2) held by the two half frames 36 and 34 (see FIGS. 6 and 3, respectively) under tension.

Reference is now made to FIGS. 18-21 which are schematic cross sectional views illustrating several steps of the assembly of a pre-tensioned implant in accordance with an embodiment of the implant assembly methods of the present application.

Figure 18:
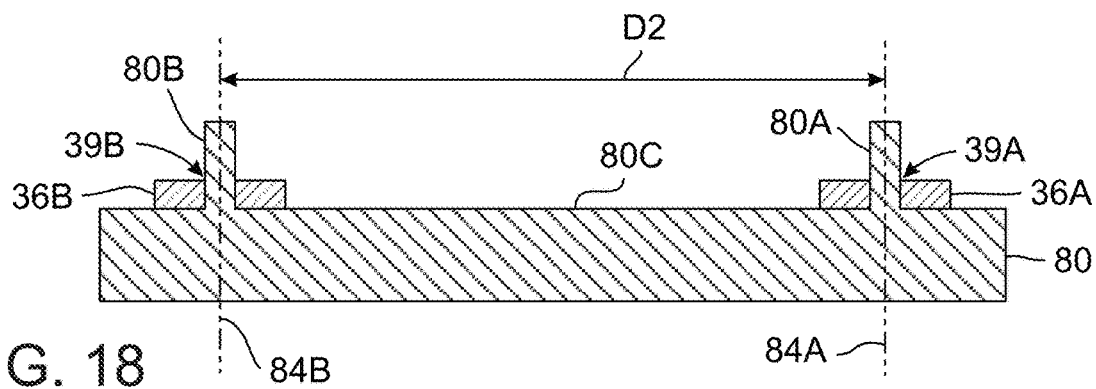
FIGS. 18, 19, 20 and 21 are schematic cross sectional views illustrating several steps of the assembly of a pre-tensioned implant in accordance with an embodiment of the implant assembly methods of the present application.

In accordance with an embodiment of the implants of the present application, a method for assembling a pre-tensioned (or pre-loaded) implant may be as follows. Turning now to FIG. 18, the first (male) half frame 36 may be compressed by applying a force thereto as explained hereinabove. When the half frame 36 is in a compressed state (as illustrated in FIG. 17) it may be (detachably) anchored to a flat plate 80 (such as, for example, a flat stainless steel plate forming the lower part of an ultrasonic welding device) such that the connecting members 35 (not seen in the cross sectional view of FIGS. 18-21) of the half frame 36 are facing upwards and away from the surface 80C of the plate 80. The plate 80 may have two straight pins 80A and 80B which may be used to anchor the first half frame 36 to the plate 80 by inserting the pins 80A and 80B into the anchoring holes 39A and 39B, respectively of the half frame 36. The anchoring of the half frame 36 by the pins 80A and 80B serves both to suitably align the half frame 36 on the plate 80 and also to hold the first half frame 36 in the compressed state since the proximal ends of the arms 36A and 36B cannot move as they are restrained by the pins 80A and 80B. The distance between the central longitudinal axes 84A and 84B of the pins 80A and 80B, respectively is D2 such that when the pins 80A and 80B are placed within the anchoring holes 39A and 39B, respectively, the half frame 36 is kept in a compressed state in which the distance between the anchoring holes 39A and 39B of the half frame 36 is D2 (as illustrated in FIG. 17).

Figure 19:
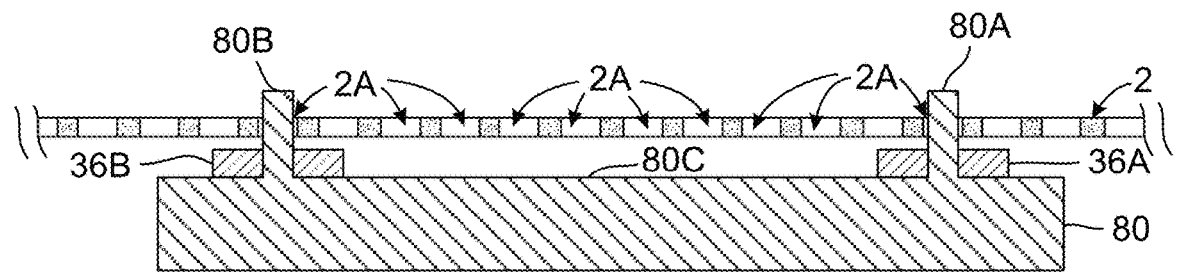
Figure 20:
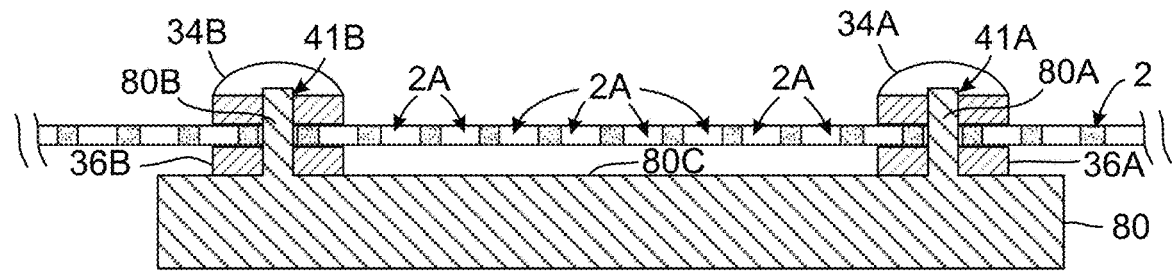
Figure 21:
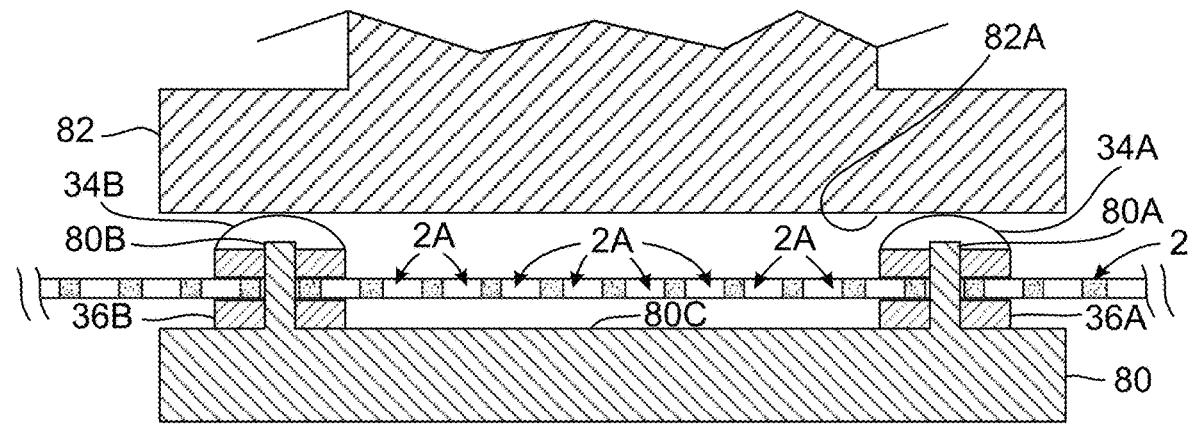

Turning now to FIG. 19, After anchoring the half frame 36 in the compressed state, the mesh 2 may be aligned and placed on the half frame 36 such that the connecting members 35 (not shown) pass through some of the openings 2A formed in the sheet 2 and protrude above the surface of the mesh 2. Turning to FIG. 20, after the mesh 2 is placed on the half frame 36, the second (female) half frame 34 may be compressed and suitably aligned and then placed on the mesh 2 by inserting the pins 80A and 80B into the anchoring holes 41A and 41B formed at the proximal ends of the arms 34A and 34B, respectively of the half frame 34 which also causes the recesses 32 (not seen in the cross sectional view of FIG. 20) to be aligned opposite the corresponding connecting members 35 of the half frame 36. Turning now to FIG. 21, After the half frame has been anchored by the pins 80A and 80B above the mesh 2 as described hereinabove, the surface 82A of an ultrasonic welding plate 82 (being part of an ultrasonic welder which is not shown in its entirety for the sake of clarity of illustration) may be placed in contact with the top surface of the half frame 34 as illustrated in FIG. 21. At this stage of the assembly of the implant, both the half frame 34 and the half frame 36 are in a compressed state while the mesh 2 is not under tension. The ultrasonic welder may now be activated to apply an ultrasonic pulse to the half frame 34 by the welding plate 82 and to lower the ultrasonic welder plate 82 for applying force to the frame 34, after the termination of the ultrasonic pulse in order to weld the connecting members 35 to the recesses 32, as disclosed hereinabove in detail with respect to the method for assembling the implant 30. After the ultrasonic welding is completed, the half frames 34 and 36 are firmly attached to each other and hold the (un-tensioned yet) mesh 2 between them.

The welding plate 82 may then be lifted off to allow access to the welded implant. When the assembled implant is lifted off the anchoring pins 80A and 80B, the restoring force exerted by the two attached half frames 34 and 36 acts on the mesh 2 and holds the mesh 2 under tension as there is some slack in the mesh 2 during assembly and due to the harnessing of the mesh 2 by the two half frames 34 and 36 and the elasticity of the mesh 2, the arms of the half frames 34 and 36 cannot return to their fully relaxed state but may only partially relax due to the restraining by the mesh 2. Therefore the assembled implant 90 is only partially relaxed and the mesh 2 is now held under tension.

After the assembled implant is taken off the plate 80, the excess of the mesh 2 which peripherally extends and surrounds the frame of the assembled implant may be trimmed to cut the mesh extending from the assembled margins of the assembled implant as disclosed in detail hereinabove with respect to the assembly of the implant 30.

Figure 22:
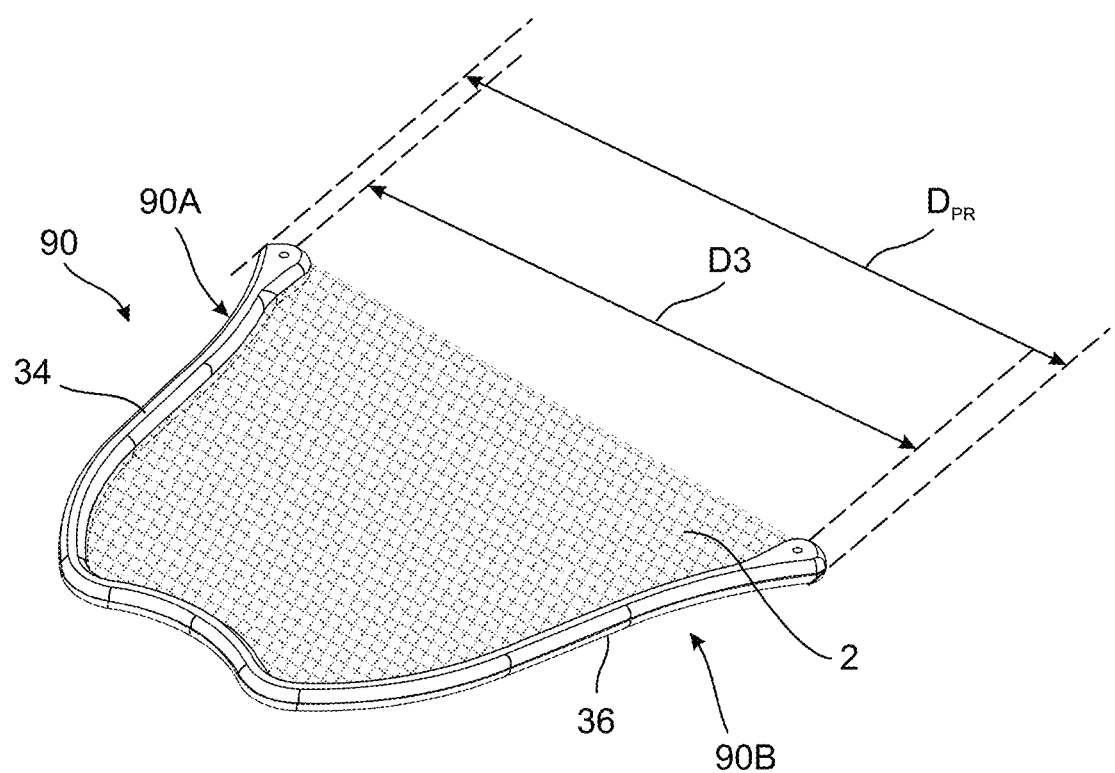
FIG. 22 is a schematic isometric view illustrating the pre-tensioned assembled implant formed using the method illustrated in FIGS. 18-21.

Reference is now made to FIG. 22 which is a schematic isometric view illustrating the pre-tensioned assembled implant formed using the method illustrated in FIGS. 18-21. The pre-tensioned implant 90 includes the half frame 34, the half frame 36 and the mesh 2 assembled together as disclosed in detail hereinabove and illustrated in FIGS. 16-21. The mesh 2 of the assembled implant 90 is held under tension as the frame of the implant 90 (comprised of the two half frames 34 and 36 firmly attached to each other, with the mesh 2 harnessed and tensioned between them) is not fully relaxed and is still compressed to a certain extent However, since the frame of the implant 90 is partially relaxed as compared to the fully relaxed state of each of the half frames 34 and 36, the distance D3 between the proximal ends of the arms 90A and 90B of the implant 90 (measured as the distance between the centers of the anchoring holes 39A and 39B) is such that D2<D3<D1 (D3 is larger than the distance D2 but smaller than the distance D1 of the fully relaxed half frames 34 and 36).

Thus, while the parts or components included in both of the implants 30 and 90 are similar, the difference between the pre-tensioned implant 90 (of FIG. 22) and the non-tensioned implant 30 (of FIG. 2) is that the distance between the proximal ends of the arms of the frames of each implant is different, being D1 in the implant 30 and D3 in the implant 90 (with D1>D2). In addition, the assembled frame of the assembled implant 90 is only partially relaxed and is restrained from fully relaxing by the mesh 2, while the frame of the assembled implant 30 is fully relaxed. Moreover, while in the implant 30 the mesh 2 is not under tension, in the pre-tensioned implant 90, the mesh 2 is held under tension.

Returning to FIGS. 3, 5, 6 and 8, it is noted that while the dimensions (in mm) of the half frames 34 and 36 represent typical dimensions of the half frame parts of an exemplary implant, they are exemplary only. Rather, the implants of the present application may have different dimensions (smaller or larger than the dimensions of the implant of FIGS. 3, 5, 6 and 8) in order to accommodate the natural anatomical variability of the pelvic region in different patients.

It was experimentally found in preliminary clinical tests that the tensioning of the mesh in pelvic implants that are pre-tensioned as disclosed hereinabove is advantageous and results in highly significant improvement of post surgical performance of pre-tensioned implants as compared to the performance of prior art (non-tensioned) mesh implants. In a preliminary clinical study in humans initiated in 2014), the pre-tensioned pelvic implants of the present application were found to have significantly improved post implantation performance as compared to prior art non-tensioned mesh pelvic implants. Briefly, as compared to the literature (FDA Meta-analysis of surgical POP devices), the safety profile of the pre-tensioned implant is potentially better than that reported for traditional surgical meshes. Short term follow up performance-wise reveals comparable results to existing pelvic organ prolapse (POP) treatment devices.

It is noted that the pre-tensioned implants of the present application as disclosed hereinabove in detail with respect to the exemplary implant 90, are not limited to implants using assembly by ultrasonic welding. Rather, the pre-tensioned implants may be made and assembled using any suitable method disclosed hereinabove with respect to any of (non-tensioned) implants 20, 30, 40, 50, 60 and 70 disclosed hereinabove as well as other types of implants disclosed in detail hereinafter (see, for example, FIGS. 23, 24 and 25). Thus, any suitable assembly method disclosed herein or known in the art may be used as long as the mesh or sheet of the implant is held under tension in the resulting assembled implant. For example, a pre-tensioned implant may be made using the mesh 2 and the two half frames 54 and 56 of FIG. 11 by using the pre-tensioning method illustrated in FIGS. 18-21 such that the half frames 54 and 56 are compressed prior to their placement on the plate 80 hand held during assembly by the pins 80A and 80B. After assembly of the mesh 2 and the compressed half frames 54 and 56, any of the nailing methods disclosed in detail hereinabove may be used, including, but not limited to, the ultrasonic nailing method, the ironing (hot plate) method, and any suitable mechanical nailing method. The resulting assembled implants will be pre-tensioned implants in accordance with additional embodiments of the pre-tensioned implants of the present application.

Similarly, an additional embodiment of pre-tensioned implants may be made from the half frames 64 and 66 of FIG. 14 by modifying the assembly method to include compressing the half frames 64 and 66 during assembly (for example, by using the plate 80 and pins 80A and 80B of FIG. 18), and mechanically attaching of the half frame 64 to the half frame 66 with the mesh 2 held and harnessed between the half frames 64 and 66, using the "snap in" method disclosed hereinabove, resulting in a pre-tensioned implant.

Similarly, an additional embodiment of pre-tensioned implants may be made from the half frames 74 and 76 of FIG. 15 by modifying the assembly method to include compressing the half frames 74 and 76 during assembly (for example, by using the plate 80 and pins 80A and 80B of FIG. 18), and mechanically attaching of the half frame 74 to the half frame 76 with the mesh 2 held and harnessed between the half frames 74 and 76, using the "snap in" method disclosed hereinabove, resulting in a pre-tensioned implant.

It is noted that the pre-tensioned implants of the present application are not limited to the specific implant assembly methods and implant components disclosed in the present application and that the pre-tensioned implants contemplated in the present application may include any type of pelvic implants, breast reconstructive implants, hernia implants and other implants in which a compressible elastic frame is attached to a sheet or a mesh such that after assembly of the implant (attachment of the sheet or mesh to the frame) the sheet or mesh is held by the frame under tension.

In the pre-tensioned implants of the present application the tension under which the sheet or mesh of the implant is held is chosen so that the mesh is stretched to prevent formation of mesh folds (such folds in the sheet or mesh may result in patient pain after implantation, and may also result in mesh erosion) on one hand, while preserving the vaginal natural elasticity. Typically, in implants having a distance between the proximal arm ends of about 90 mm (in the fully relaxed state of the frame) a "preload" of about 10 mm may be typically (but not obligatorily) used. The preload P (which is related to the force under which the mesh is held in the partially relaxed state of the implant after assembly of the implant) is defined as the shortening (in mm) of the distance between the lateral sides of the proximal ends of the frame's arms when the frame is in a compressed state during assembly. For example, for a pre-tensioned implant 90 of FIG. 22 which comprises the half frames 36 and 34, the distance between the lateral sides of the proximal ends of the half frame arms 36A and 36B during the fully relaxed state is $D_{FR}$ (see FIG. 16), while the distance between the lateral sides of the proximal ends of the half frame arms 36A and 36B during the compressed state (when the half frame 36 is held compressed by the pins 80A and 80B of FIG. 18 during assembly of the implant 90) is $D_C$ (see FIG. 17), and the distance between the lateral sides of the proximal ends of the frame arms 90A and 90B in the partially relaxed state is $D_{PR}$ (see FIG. 22). Thus, for the specific example of the implant 90, $P=D_{FR}-D_C=88.9$ mm-78.9 mm=10 mm. After assembly of the implant 90 is completed and the assembled implant 90 is allowed to partially relax as explained in detail hereinabove, $D_{PR}$ is typically measured to be 82-83 mm. From empirical measurements it was found that the force exerted on the mesh 2 by the arms of the implant 90 at the partially relaxed state is about 0.5 Newton which satisfactorily prevents folding of the mesh 2 and mesh erosion after implantation while preserving the vaginal natural elasticity after implantation of the implant 90 in the pelvis.

It is noted that the while the preloading of 10 mm is typically suitable for the specific exemplary implant 90, different preloading values (smaller or larger than 10 mm) may be used in other different types of pre-tensioned implants of the present application, depending, inter alia, the mechanical properties of the mesh or sheet being used in the implant, and on the degree of tension in the sheet practically sufficient to prevent formation of folds in the sheet while not resulting in adverse effects due to excessive limitation of the vaginal elasticity.

Similarly, it is noted that the force $F_{PR}$ exerted on the mesh (or sheet) by the partially relaxed frame after assembly of the implant is not limited to 0.5 Newton and may be higher or lower than 0.5 Newton, depending, inter alia, on the specific dimensions and configuration of the implant, the elasticity of the materials from which the frame and the mesh (or sheet) of the implant are made, the mechanical properties of the mesh or sheet being used in the implant, and the preload P being used. Typically, the force $F_{PR}$ may be in the range of 0-2 Newton. However, the above indicated rage is not obligatory and a force $F_{PR}$ higher or lower than the values of this range may be used in some implants.

It is noted that the implants of the present application are not limited to the implants having two half frames as disclosed hereinabove. For example, the implants disclosed herein may include a "monolithic" frame (a single unit frame) and may be assembled using assembly methods different from the methods disclosed hereinabove.

Figure 23:
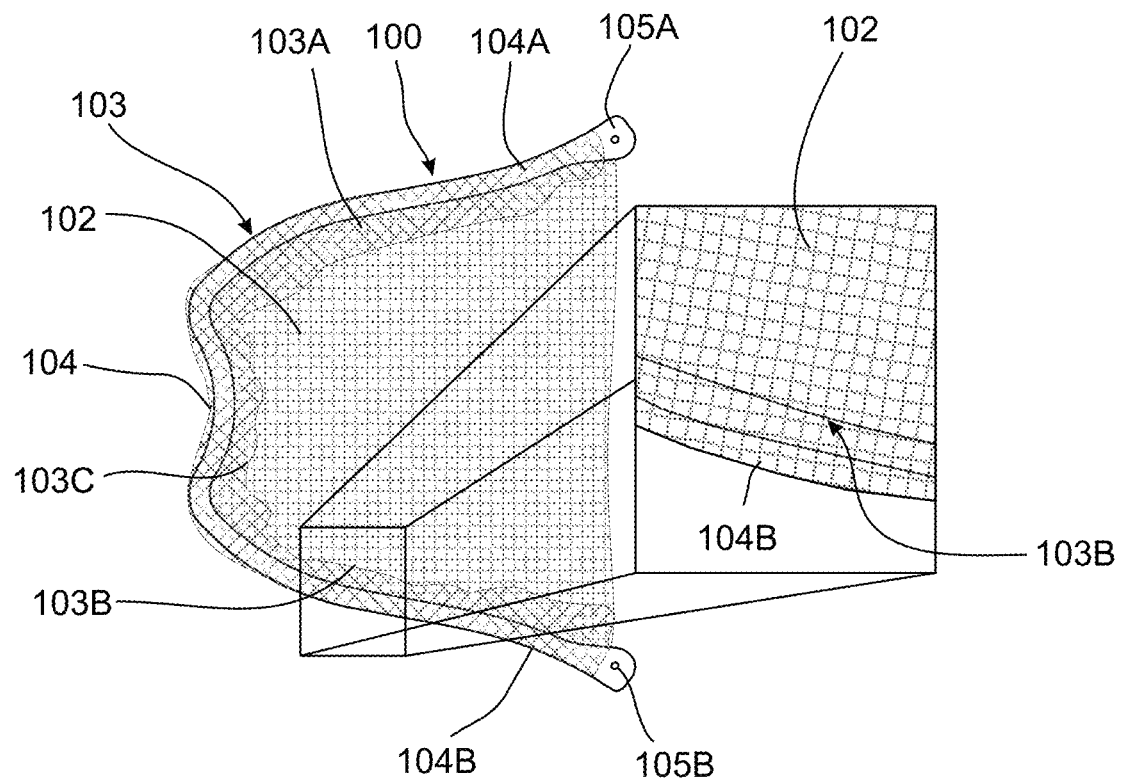
FIG. 23 is a schematic top view illustrating an implant having a monolithic frame and a mesh or sheet including sleeves, in accordance with another embodiment of the implants of the present application.
Figure 24:
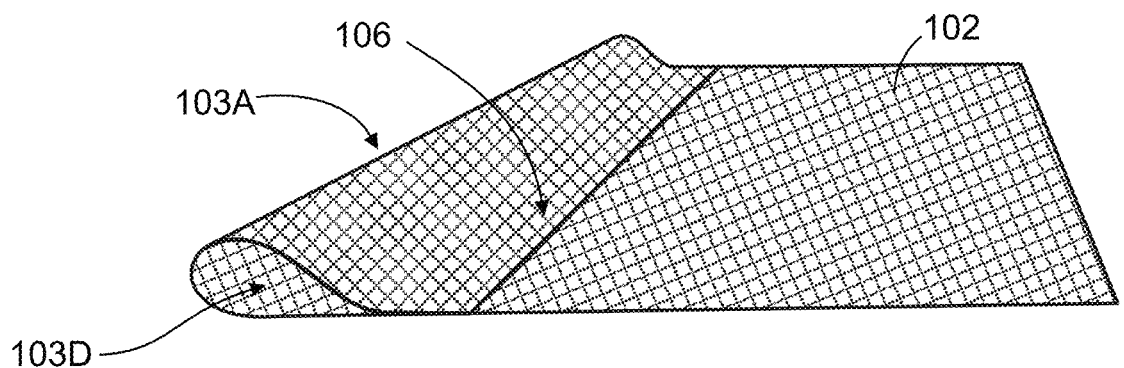
FIG. 24 is a schematic isometric view of part of a sheet suitable for use in some of the implants of the present application.

Reference is now made to FIGS. 23-24. FIG. 23 is a schematic top view illustrating an implant having a monolithic frame and a mesh or sheet including sleeves, in accordance with another embodiment of the implants of the present application. FIG. 24 is a schematic isometric view of part of a sheet suitable for use in some of the implants of the present application. Turning to FIG. 23, the implant 100 includes a frame 104 which is a flexible and elastic frame. The frame 104 may be made from any of the elastic materials or combination of materials as disclosed hereinabove in detail for the implant 20 and 30. The implant 100 also includes a sheet 102 (such as a mesh, a divider, as disclosed in detail hereinabove, a multi layered sheet, and a coated sheet), the sheet 102 may be any sheet or mesh made from any of the materials disclosed hereinabove for the sheet 2.

The sheet 102 may be attached to the frame 104 by providing a piece of sheet having a perimeter which is larger in size than the perimeter of the frame 104 and by suitably folding the peripheral edges of the sheet 2 over the frame 104 towards the inside of the sheet region circumscribed by the frame 104 until they are in contact with the surface of the region of the sheet 102 lying inside of the frame 104 and then firmly attaching the folded edges of the sheet 102 to the portions of the sheet 102 disposed inside of the frame 104. The folding over and attaching of the sheet 102 parts to each other forms a sleeve (such as for example the sleeve 103 including the sleeve portions 103A and 103B disposed on opposing lateral sides of the sheet 102 and the sleeve portion 103C disposed on the distal portion of the sheet 102. The attaching of the folded sheet 102 to form the sleeve 103 may be performed by any suitable attaching method known in the art. For example, the attaching may be performed by ultrasonic welding (using an appropriate ultrasound pulse to avoid damage to the sheet 2), by ironing using a hot plate, by gluing (using a suitable biocompatible glue), by suturing or stitching, or by any other type of suitable attaching method known in the art.

The frame 104 is in this way enclosed within the sleeve 103 and supports the sheet 102. The implant 100 may be a non-tensioned implant if the frame 104 is fully relaxed during the assembly of the implant. However, in accordance with another embodiment of the implants of the present application, the implant 100 may formed as a pre-tensioned implant by compressing the elastic frame 104 and performing the folding of the sheet 102 while the frame 104 is held in a compressed state. Such holding of the frame 104 in a compressed state may be performed by using a plate similar to the plate 80 disclosed hereinabove and illustrated in FIG. 18 and inserting the pins 80A and 80B into respective openings 105A and 105B formed in the proximal ends of the arms 104A and 104B of the frame 104 to retain the frame 4 in a compressed state during the assembly of the implant 100.

Alternatively and/or additionally, any other suitable methods may be used to hold the frame 104 in a compressed state, including, for example, forming a suitable shaped recess (not shown) in the plate on which the implant is assembled such as to accommodate and hold the shape of the frame 104 while it is in the proper compressed state. Such a shaped recess will hold the compressed frame in place in its compressed state while assembly of the implant 100 is carried out as detailed hereinabove. In this method it may actually be easier to fold the sheet 102. In the recessed plate method, the frame 104 is held in the compressed state during assembly. The sheet 102 may be placed on such a recessed plate and the frame 104 may be compressed and then pushed over the sheet 102 and into the shaped recess of the plate until it fits within the shaped recess. As a result of the fitting of the frame 104 within the recess, the sheet 102 is forced to align with the external wall of the shaped recess and partially folds making it easy to complete the folding of the sheet 102 over the frame 104. The assembly of the pre-tensioned implant may then be completed by attaching the folded perimeter of the sheet 102 to the surface of the sheet 102 circumscribed within the frame 104 by any of the attachment methods disclosed hereinabove. Turning to FIG. 23, a portion of the sheet 102 is illustrated (without the frame 104 being shown, for the sake of clarity of illustration). The sleeve portion 103A is illustrated as having an internal passage 103D for accommodating the respective portion of the frame 104 (not shown). The region of attachment 106 of the sheet 102 to itself forming the sleeve is schematically illustrated in FIG. 24.

In accordance with another method of assembly of the implants, the sleeves (or at least some of the sleeve portions) of the sheet 102 may be formed prior to the assembly of the implant. For example, the lateral sleeve portions 103A and 103B may be formed in the sheet 102, prior to assembling the implant 100 by any of the suitable sleeve forming methods disclosed hereinabove. The frame 104 may then be added by compressing the frame 104 and then inserting the proximal end of the arm 104A into the opening 103D of the sleeve portion 103A and inserting the proximal end of the arm 104B into the opening of the sleeve portion 103B. After the arms 104A and 104B are fully inserted into the sleeve portions 103A and 103B, respectively, the frame 104 may be allowed to partially relax, tensioning the sheet 102. The sleeve portion 103C (of FIG. 23) may then be formed by folding a portion of the sheet 102 extending at the distal part of the sheet 102 over the distal part of the frame 104 and attaching that portion of the sheet 102 to the surface of the sheet 102 on the region inside the frame 104 and adjacent the distal portion of the frame 104 by any of the sleeve forming method disclosed hereinabove to form the sleeve portion 103C which completes the harnessing of the sheet 102 to the frame 104 and prevents detachment of the sheet 102 from the frame 104 after implantation in the pelvis. It is noted that the sleeve portion 103C is not mandatory and that in other embodiments having a sheet with sleeves, the mesh the distal portion of the sheet or mesh need not be attached to the frame of the implant (such as, for example, is the implant 130 of FIG. 25, hereinafter.

Figure 25:
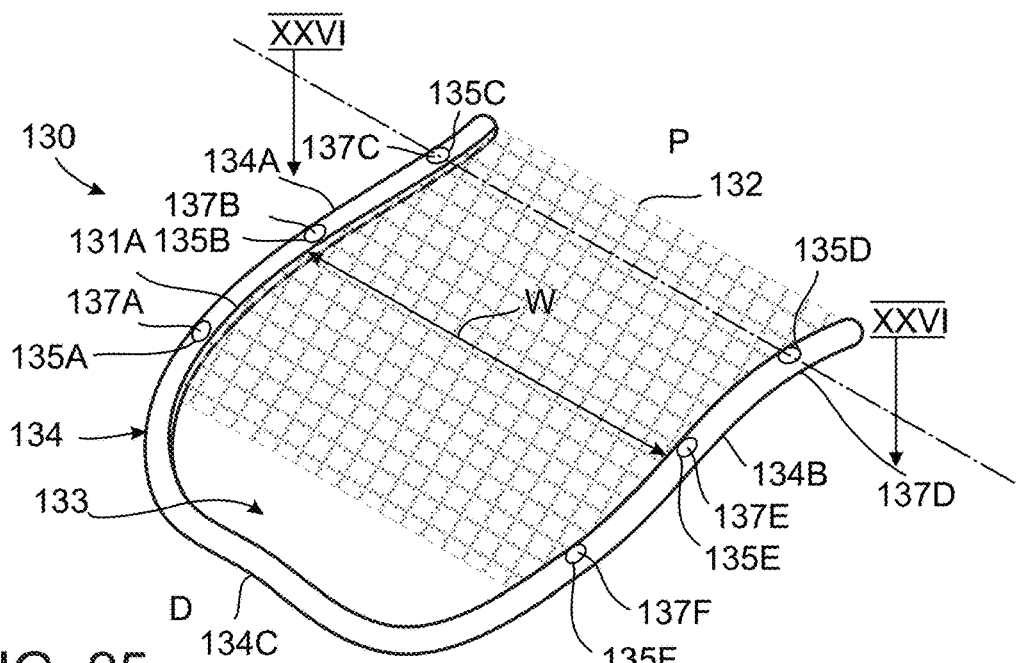
FIG. 25 is a schematic isometric view illustrating an implant in accordance with yet an additional embodiment of the implants of the present application.
Figure 26:
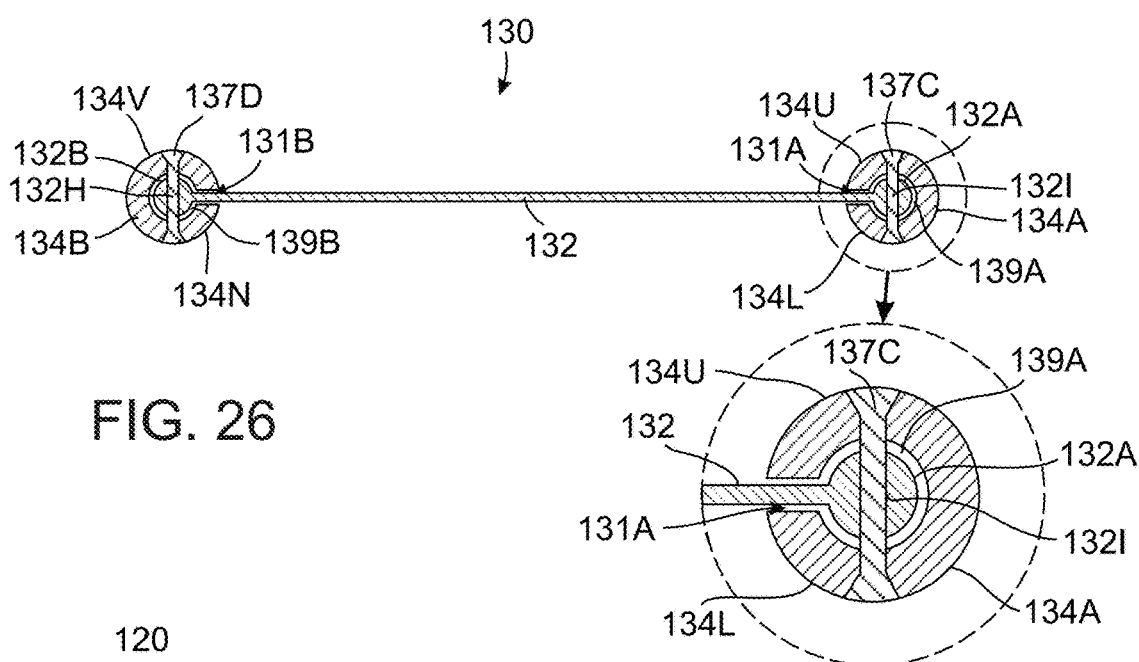
FIG. 26 is a schematic cross sectional view of the implant of FIG. 25 taken along the lines XXVI-XXVI.

It is noted that the use of a monolithic frame in the implants of the present application is not limited to the type of frame and sheet structure illustrated in FIGS. 23-24. Reference is now made to FIGS. 25-26. FIG. 25 is a schematic isometric view illustrating an implant in accordance with yet an additional embodiment of the implants of the present application. FIG. 26 is a schematic cross sectional view of the implant of FIG. 25 Taken along the lines XXVI-XXVI. Turning now to FIG. 25, the implant 130 includes a monolithic open frame 134 and a mesh 132 attached to the frame 134. The frame 134 has two arm portions 134A and 134B ending at the proximal open end of the frame 134 and a distal portion 134C extending between the arm portions 134A and 134B. The frame 134 comprises two longitudinally extending hollow passages 139A and 139B. The longitudinal passage 139A extends along part of the length of the arm portion 134A and is an open passage having a slit-like opening 131A opening on the side surface of the arm portion 134A facing the arm portion 134B. The longitudinal passage 139B extends along part of the length of the arm portion 134B and is an open passage having a slit-like opening 131B opening on the side surface of the arm portion 134B facing the arm portion 134A. The arm portion 134A may have three small open passages 135A, 135B and 135C passing through the entire thickness of the arm portion 134A from its upper surface 134U through the hollow longitudinal passage 139A and exiting from the lower surface 134L of the arm portion 134A (best seen in detail in FIG. 26). The arm portion 134B may have three small open passages 135D, 135E and 135F passing through the entire thickness of the arm portion 134B from its upper surface 134V through the hollow longitudinal passage 139B and exiting from the lower surface 134N of the arm portion 134B (best seen in detail in FIG. 26).

The mesh 132 is a rectangular mesh and has two longitudinally extending elongated attachment members 132A and 132B formed along two opposite sides of the mesh 132. When the mesh 132 is attached to the frame 134, the elongated attachment members 132A and 132B extend in the proximal-distal direction of the implant, as marked by the letters P (for proximal end of the implant 130) and D (for the distal end of the implant 130). The elongated attachment member 132A may have three open passages formed therein, each open passage of the elongated attachment member 132A may have a diameter identical to the diameter of the corresponding open passages 135A, 135B and 135C of the arm portion 134A to allow three attachment pins 137A, 137B and 137C to pass therethrough for attachment and securing of the elongated attachment member 132A within the longitudinal passage 139A of the arm portion 134A. The elongated attachment member 132B may have three open passages formed therein, each open passage of the elongated attachment member 132B may have a diameter identical to the diameter of the corresponding open passages 135D, 135E and 135F of the arm portion 134B, to allow three attachment pins 137D, 137E and 137F to pass therethrough for attachment and securing of the elongated attachment member 132B within the longitudinal passage 139B of the arm portion 134B.

It is noted that due to the cross-sectional view of FIG. 26, only the open passages 132I of the elongated attachment member 132A and the open passages 132H of the elongated attachment member 132B are seen in FIG. 26. Turning to FIG. 26, when the implant 130 is being assembled, the elongated attachment member 132A of the mesh 132 may be inserted into the longitudinal passage 139A of the arm portion 134A through an opening in the proximal end of the arm portion 134A (the opening cannot be seen in the isometric view of FIG. 25) and the elongated attachment member 132B of the mesh 132 may be inserted into the longitudinal passage 139B of the arm portion 134B through an opening in the proximal end of the arm portion 134B (the opening cannot be seen in the isometric view of FIG. 25). The mesh 132 may then be pushed (or alternatively pulled distally, such that the flat portion of the mesh 132 slides through the slit-like openings 131A and 131B of the hollow longitudinal passages 139A and 139B, respectively, until the mesh 132 is positioned such that the three open passages of the elongated attachment members 132A are aligned with the corresponding open passages 135A, 135B and 135C and the three open passages of the elongated attachment members 132B are aligned with the corresponding open passages 135D, 135E and 135F. The six securing pins 137A-137F are then inserted through the openings 135A-135F, respectively and expanded at both of their ends (for example, by mechanically nailing both ends of the securing pins or by thermally expanding both ends of the securing pins or by any other method known in the art for attaching a securing pin), in a similar way to the methods of expanding of the connecting members 55 (of FIG. 11) The securing pins 137A-137F may also have a diameter that is slightly larger than the diameter of open passages 135A-135F and may be forced into the open passages 135A-135F under strain. Alternatively, the securing pins 137A-137F may be threaded or screw-like in shape and may be screwed into the open passages 135A-135F (and the open passages 132I and 132H).

After the securing pins 137A-137F are fixedly attached and firmly secured to the arm portions 134A and 134B, the mesh 132 is securely and firmly attached within the frame 134. It is noted that the number of the securing pins need not be six but may be smaller or larger than six. Furthermore, while the elongated attachment members 132A and 132B preferably have a circular cross section and the two longitudinally extending hollow passages 139A and 139B preferably have a generally circular (hollow) cross sectional shape to receive the elongated attachment members 132A and 132B therein, this is not obligatory and the cross sectional shapes of longitudinally extending hollow passages 139A and 139B and of the elongated attachment members 132A and 132B may be of any suitable shape (such as, for example, elliptical shape, T-shape, rectangular shape, polygonal shape, or any other suitable shape) as long as the shape is suitable to effectively hold the elongated attachment members 132A and 132B captive within the longitudinally extending hollow passages 139A and 139B, respectively, after assembly of the implant and after implantation in the body.

It is noted that, as may be seen in FIG. 25, the rectangular (or nearly rectangular) mesh 132 does not span the entire area defined by the frame 134 and the region 133 at the distal end is not covered by the mesh 132. This does not adversely affect the performance of the implant 130 but makes it easier and more convenient to attach the mesh 132 to the frame 134 without causing undesired formation folds in the mesh 132. It is further noted that while the frame 134 may be a flat frame, other embodiments of implants using a mesh attachment method similar to the attachment method disclosed with respect to the implant 130 may include curved frames (such as, for example, the curved frame 124 of the implant 120 illustrated in FIG. 27 hereinafter). Additionally, the implant 130 may be a non-tensioned implant but may also be assembled as a pre-tensioned implant by suitably selecting the width W of the rectangular mesh 132 such that is smaller than the distance between the arm portions 134A and 134B when the frame 134 is fully relaxed. When such a pre-tensioned implant is assembled, the frame 134 is first compressed and held in a compressed state and the mesh 132 is then attached to the frame as disclosed in detail hereinabove and secured with the securing pins 137A-137F as disclosed hereinabove. After assembly, the frame is allowed to expand but may only partially relax due to the restraining by the shorter width of the mesh 132, resulting in a pre-tensioned implant.

Similarly, the implant 130 may be modified by including therein two additional distally extending arms and a second strap-like mesh (such as, for example, the arms 164C and 164D and the second mesh 168 of FIG. 30 hereinafter), and/or by including therein additional portions or parts of the arms 134A and 134B that are bent towards each other at an angle α (such as, for example, the bent arm portions 144D and 144E of the implant 140 of FIG. 29, hereinafter).

It is also noted that the method of fixating or securing the mesh 132 to the frame, is not limited to using securing pins and corresponding passages in the arms of the frames as illustrated in FIG. 25. Rather, any other suitable type of method, known in the art for attaching the mesh 132 firmly to the frame 134 may be used. For example, crimping, riveting, gluing with a biocompatible glue, or any other suitable type of securing method known in the art may be used to attach the mesh 132 to the frame 134 to prevent longitudinal sliding of the elongated attachment members 132A and 132B within the longitudinally extending hollow passages 139A and 139B, respectively.

It is noted that while in the implants 20, 30, 50, 60 and 70 disclosed hereinabove, the frame of the implant holding the sheet or mesh is flat frame resulting in a substantially flat (planar) implant, this is not obligatory for practicing the invention. The inventor of the implants of the present application has invented an additional embodiment of the implants which further improves the performance of pelvic implants. One of the problems encountered in the use of flat or planar implants is that such implants under the forces applied to the implant by prolapsing organs (such as, for example the bladder and or urethra) may be pushed downward towards the vagina which may result in pain to the patient and may compromise the natural vaginal elasticity. It was found that by suitably curving the frame of the implants it is possible to provide a significantly better fit of the implants to the naturally occurring curvature of the space defined between the vaginal outer surface and the surfaces of the bladder and urethra overlying the vagina.

Figure 27:
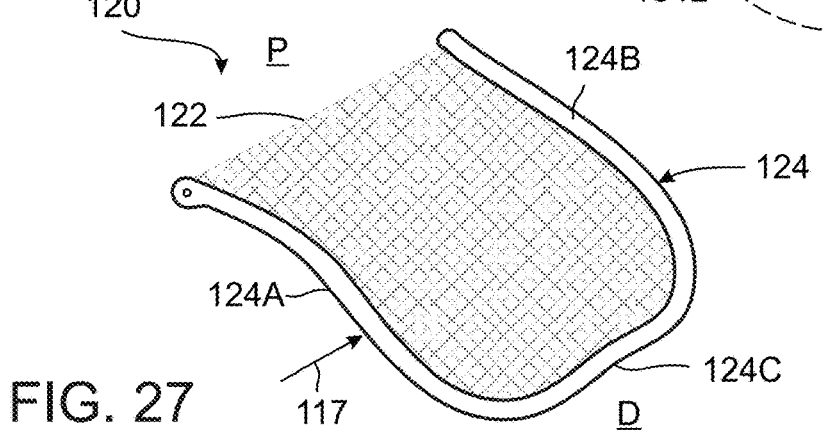
FIG. 27 is a schematic isometric view illustrating a curved pelvic implant, in accordance with yet another embodiment of the implants of the present application.
Figure 28:
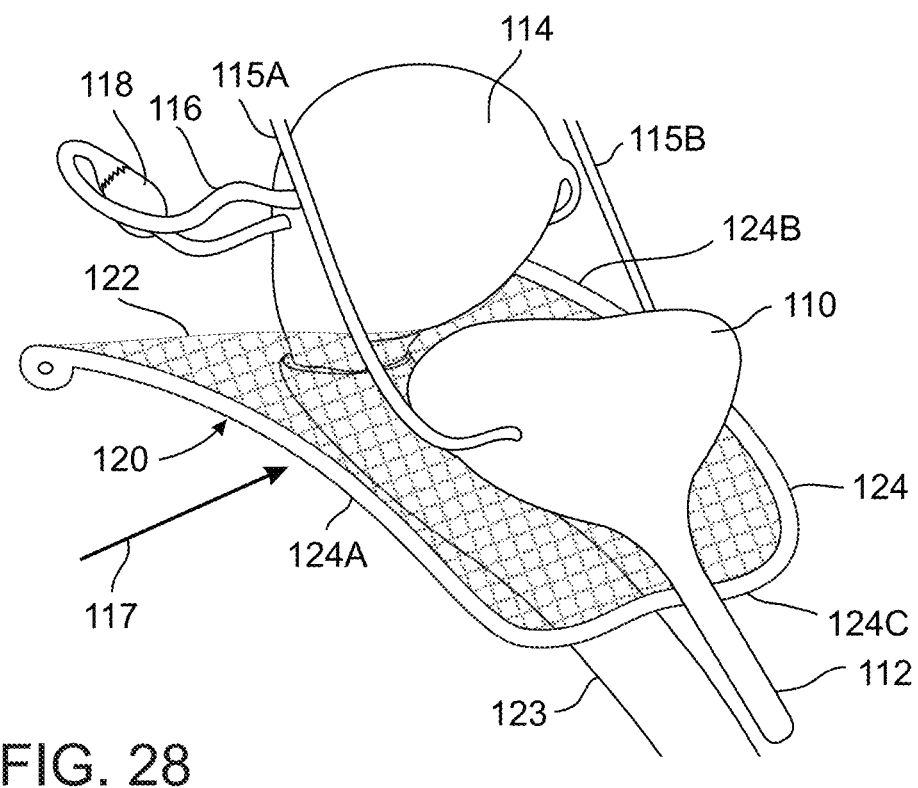
FIG. 28 is a schematic isometric view illustrating the implant of FIG. 27 disposed between a bladder and urethra and a vagina of a human female pelvis after implantation.

Reference is now made to FIGS. 27-28. FIG. 27 is a schematic isometric view illustrating a curved pelvic implant, in accordance with yet another embodiment of the implants of the present application. FIG. 28 is a schematic isometric view illustrating the implant 120 of FIG. 27 disposed between a bladder and urethra and a vagina of a human female's pelvis after implantation.

The implant 120 comprises a frame 124 and a sheet 122 firmly attached to the frame 124. The frame 124 may be an open frame and has a distal (closed) side represented in FIG. 26 by the character "D" and a proximal (open) side represented in FIG. 26 by the character "P". The frame124 has two arm portions 124A and 124B and a contoured distal portion 124C. The frame 124 is a flexible elastic frame and may be made from any of the materials disclosed hereinabove with respect to the frames of the implants 20 and 30 of FIGS. 1 and 2, respectively. The mesh 122 is a soft and flexible mesh which may be made from any of the materials disclosed hereinabove for making the mesh 2 of FIGS. 1 and 2. For example, the frame 124 may (optionally) be made from PEEK and the mesh 122 may be made from PP, as disclosed hereinabove.

The mesh 122 may be attached to the frame 124 by using any of the mesh (or sheet) attachment methods disclosed hereinabove with respect to any of the implants disclosed hereinabove with suitable modification of the method to allow for the curved form of the implant. While the flat (planar) implants disclosed hereinabove may be laterally contoured to better fit the implant in the pelvis after implantation (as best seen in FIGS. 1-3), in the implant 120 the portions 124A and 124B of the frame 124 may be contoured laterally and are also curved such that the frame 124 is non-planar (not flat) in structure such as to achieve a better fit of the implant 120 in the curved space between the bladder and the vagina. If the frame 124 is viewed from a lateral side (such as, for example, in the direction of the arrow 117, the arm portions 124A and 124B are seen as curved rostro-caudally and have a convex shape such that the frame 124 is not flat (not planar).

When the mesh 122 is attached to the curved arm portions 124A and 124B, the curvature results in the mesh 122 also being curved in three dimensional (3D) space resulting in a generally "saddle like" shape. The precise shape of the mesh 122 in three dimensional space may depend, inter alia, on the dimensions of the frame 124, the state of the mesh 122 (tensioned or not tensioned by the frame 124), the tension or forces exerted by the frame 124 on the mesh 122, if the mesh 122 is pre-tensioned), the elasticity of the frame 124 and of the mesh 122, and on other mechanical parameters such as the type and structure of the attachment of the mesh 122 to the frame 124. However, The overall fit of the implant 120 within the curved space available between the bladder and urethra and the vagina is significantly better than the fit of any of the flat implants disclosed hereinabove (such as, for example, the implants 20 and 30).

Turning to FIG. 28, after implantation, the implant 120 is disposed in the space defined between the bladder 110 and urethra 112 and the vagina 123. An ovary 118, a fallopian tube 116 and the urethers 115A and 115B entering the bladder 110 are illustrated for the purpose of clarifying the local female pelvic anatomy in relation to the implant's positioning. Due to the space between the above organs being curved and the curvature of the implant 120 which is shaped to follow the curvature of the space between these organs, the implant 120 reduces or even eliminates any pressure on the bladder, urethra and the vagina by the sheet or mesh being used in the curved implant and may reduce the incidence of post implantation complications such as limiting or reducing the vaginal elasticity with the accompanying patient discomfort, and/or stress urinary incontinence (SUI), as compared to the incidence of such complications when flat implants are being used.

It is noted that the frame 124 of the implant 120 may be constructed using any of the frame construction types, disclosed hereinabove for any of the flat implants of the application. For example, the frame 124 may be made from two suitably curved frame halves (not shown in FIG. 27) attachable to each other with the mesh 122 harnessed and held between the two complementary frame halves. Such curved frame halves may be firmly attached to each other to form the frame 124 by using any of the attachment methods disclosed hereinabove for the flat implants (such as, but not limited to, thermal bonding methods, ultrasonic welding, ironing, nailing methods and any other attachment method making use of connecting members and matching recesses and/or openings, and any other mechanical attachment methods known in the art such as "snap in", mechanical nailing connector members and gluing).

It is further noted that the frame 124 may be formed as a monolithic frame and the mesh 122 may be attached to the frame by folding and attachment of suitable portions of the mesh 122 to form one or more sleeves enfolding the arm portions 124A and 124B therein (and, optionally, also the frame portion 124C in some embodiments). It may also be possible to use a curved monolithic frame (not shown in detail) having a suitably shaped longitudinal recess formed therein to receive and hold captive a suitably shaped margin portion formed on the perimeter of the mesh 122 similar to the attachment method illustrated to the flat implant of FIGS. 25-26.

Furthermore, the curved implants of the present application may be non-tensioned but may also (preferably) be pre-tensioned curved implants in which the frame of the implant is compressed during implant assembly and partially relaxed after assembly, exerting a force of the mesh 122 to hold the mesh of the implant under tension.

When assembling such a curved pre-tensioned implant including a curved male half frame and a curved female half frame by using an ultrasonic welding method, the plates of the ultrasonic welding jig may have to be suitably curved to enable accommodating the curved implant parts during the implant assembly.

Similar modifications may have to be made to any assembly jig used assembling a curved implant by any of the assembling methods disclosed hereinabove with respect to assembling different types of flat implants. For example, a suitably curved base plate and a suitably curved ironing hot plate may have to be used to assemble curved implants having matching curved half frames attachable by any of the types of nailing methods disclosed hereinabove. Similarly, a suitably curved ultrasonic jig plate or plated may have to be used for ultrasonically welding a curved implant having two curved half frames as disclosed hereinabove. Such modification of assembly jigs by replacing the flat plates having planar surfaces (such as, for example, the lower plate 80 and the welding plate 82 of FIGS. 18-21) of any of the above disclosed assembly jigs by plates or other members having suitably curved surfaces for accommodating the curvature of the implant or the curvature of any curved half frames being used to assemble the curved implant, will be easily constructed and operated by the person skilled in the art without undue experimentation.

It is noted that the curvature of any of the curved implants of the present application may be adapted to the type and arrangement of organs between which the sheet or mesh of the implant is disposed. For example, if the curved implant is implanted between a vagina and a bladder, the curvature of the implant's arms may be configured to fit the natural curvature between the bladder and the vagina. If the implant is to be implanted between a vagina and a rectum (in a para-rectal compartment) of a patient, the curvature of the arms of the implant may be configured to fit the natural curvature between the rectum and the vagina.

Figure 29:
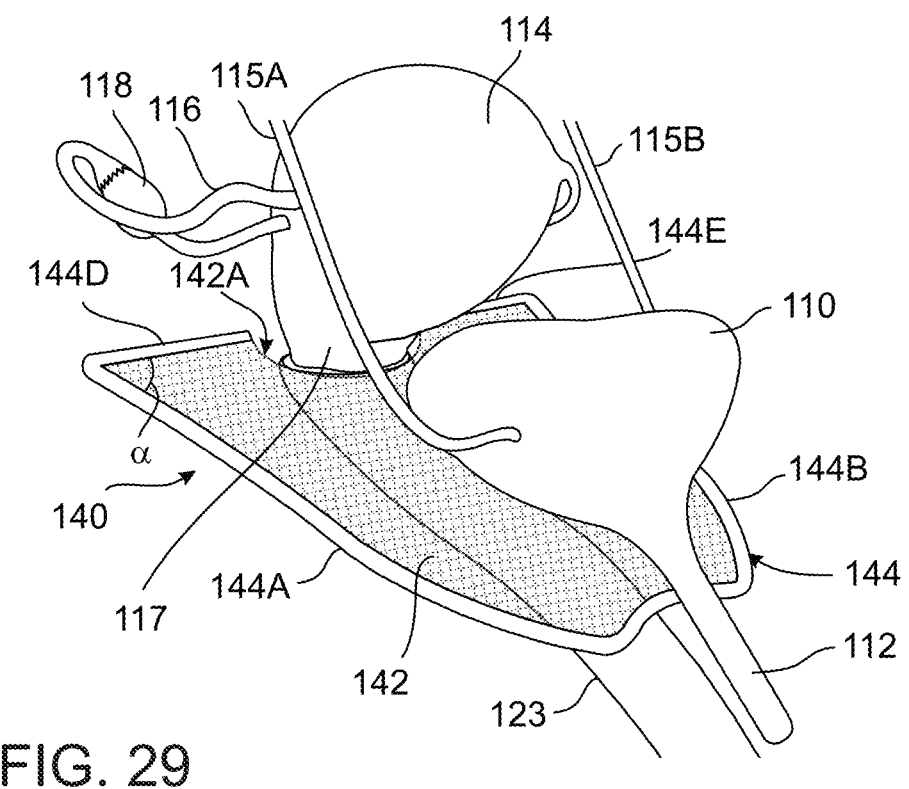
FIG. 29 is a schematic isometric view illustrating a pre-tensioned implant having bent arms, in accordance with yet another embodiment of the implants of the present application.

Reference is now made to FIG. 29 which is a schematic isometric view illustrating a pre-tensioned implant having bent arms, in accordance with yet another embodiment of the implants of the present application. The implant 140 includes a frame 144 and a mesh 142 firmly attached to the frame 144. The frame 144 is generally similar in shape to the frame 4 of FIG. 1 except that the proximal ends 144D and 144E of the lateral frame arms 144A and 144B, respectively are bent at an angle towards each other.

The bent proximal ends 144D and 144E of the frame 144 may be implemented as integral portions of the frame 144 or alternatively may be implemented as separate parts of the frame 144 and may be attached to the portions 144A and 144B of the frame by any suitable attachment method known in the art (such as, for example, welding, thermal bonding, gluing, and snap-in mechanical connectors). The mesh 142 may be similar to the sheet 2 of the implant 30 except that it may (optionally) include semi-circular notch 142A formed therein to better accommodate the cervix of the uterus 114. However, in other embodiments of the implant of FIG. 28, the proximal end of the mesh 122 may be similar to the proximal end of the sheet 2 of FIG. 1 and does not include the notch 142A. The bent proximal ends 144D and 144E of the frame 144 may improve the harnessing of the mesh 142 and may provide better support of the mesh 142 by the frame 144. Additionally, the partial closing of the wide proximal opening at the proximal end of the implant 140 by the bent proximal portions 144D and 144E provides better support to the cervix 117 and/or the uterus 114 which are located at the proximal edge of the mesh 142. The extensions (bent proximal ends) of the frame arms provide support to the vaginal apex or cervix since they are located in the most proximal part of the device. Such bent proximal ends of the frame's arms are configured to simulate the cardinal ligaments which provide lateral support to the uterus.

It is noted that the length of the bent proximal portions 144D and 144E are not limited to the length illustrated in FIG. 29. Rather, the length of the bent proximal portions 144D and 144E may be of any suitable length to adapt the implant to any natural anatomical variation of the female uterus and cervix. Furthermore, the bent portions 144D and 144E may be extended such that they almost touch each other or even such that they do touch each other, depending, inter alia, on the particular medical application for which the implant is intended.

It is noted that while the angle α (alpha) between the portion 144A and 144D and between the portion 144B and 144E, may be a right angle as illustrated in FIG. 28, in other embodiments of the implants, the angle α may also be an acute angle (smaller than 90 degrees) or an obtuse angle (larger than 90 degrees).

It is further noted that any of the flat implants disclosed hereinabove (such as, but not limited to, the implants 20 and 30) may also be modified to include bent portions disposed at the proximal ends of the arms of the frame of the implant to improve support of the mesh or sheet of the implant and consequently the support of pelvic organs.

Figure 30:
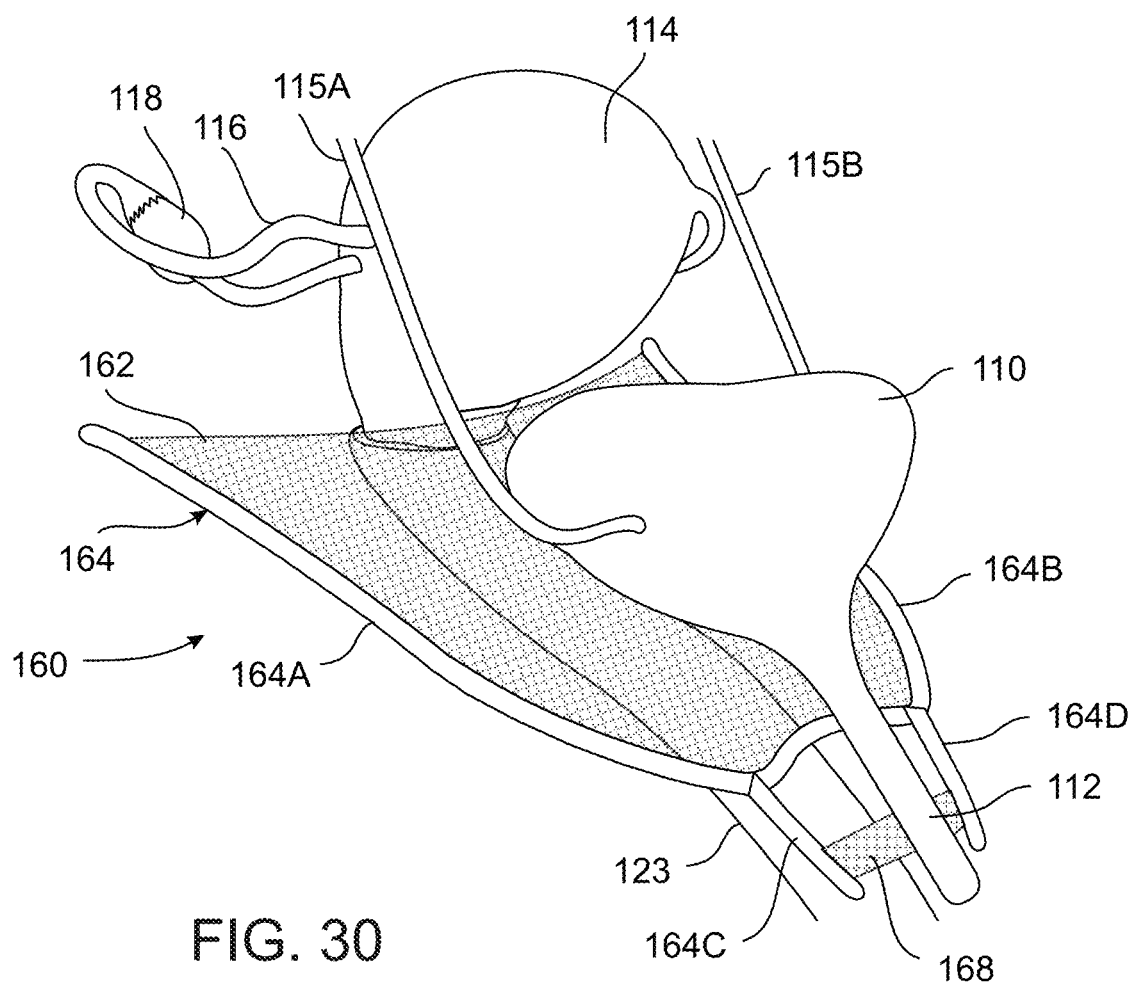
FIG. 30 is a schematic isometric view, illustrating an implant giving four arms, in accordance with another embodiment of the implants of the present application.

Reference is now made to FIG. 30 which is a schematic isometric view, illustrating an implant having four arms, in accordance with another embodiment of the implants of the present application. The implant 160 includes a frame 164, a first sheet 162 and a second sheet 168. The frame 164 includes a first arm 164A, a second arm 164B, a third arm 164C and a fourth arm 164D. The first arm 164A and the second arm 164B are firmly attached to the first sheet 162 and harness and support the first sheet 162. The third arm 164D and the fourth arm 164E are firmly attached to the second sheet 168 and harness and support the second sheet 168, therebetween. The frame 164 may be made from any of the flexible elastic materials disclosed hereinabove with respect to the frame 4 of FIG. 1, and the sheets 162 and 168 may be made from any of the materials disclosed hereinabove with respect to the sheet 2 of the implants 20 and 30. The second sheet 168 may (optionally) be shaped as a strap. After implantation, the second sheet 168 may be disposed between the vagina 123 and the urethra 112 for supporting the urethra. The first sheet 162 may be shaped similar to the shape of the sheet 2 of the implants 20 and 30. In use, the frame 164 may have a first configuration in which the frame is compressed, causing the first sheet 162 and the second sheet 168 to be in a non-tensioned state, and a second configuration in which the frame 164 is expanded (relaxed), to allow the first sheet 162 and the second sheet 168 to be in a tensioned state.

After implantation of the implant 160, the first sheet 162 may be disposed, between the vagina 123 and the bladder 110 for supporting the prolapsed bladder 110. The implant 160 may be particularly well suited for implantation in cases of patients suffering from stress urinary incontinence (SUI) combined with pelvic organ prolapsed (POP). As the strap-like second sheet 168 is disposed under and support the urethra 112. Typically, in cases of SUI, increased intra-abdominal pressure may cause hypermobility of the urethra 112 leading to urine leakage. The improved support of the urethra 112 provided by the second sheet 168 of the implant 160 may therefore reduce or eliminate urine leakage in cases of stress urinary incontinence, while the support of the bladder 110 by the first sheet 162 may stabilize the prolapsed bladder 110.

It is noted that any of the suitable methods for implant assembly disclosed hereinabove may be adapted for use in constructing the implant 160 disclosed hereinabove. Thus, the frame 164 may be a monolithic frame and the first sheet 162 and second sheet 168 may have suitable sleeves formed therein, such that the first arm 164A and the second arm 164B may be held within the sleeves formed in the first sheet 162 and the third arm 164D and the fourth arm 164E may be held within sleeves formed in the second sheet 168 in a way similar to the attachment of the frame arms 104A and 104B of the implant 100 are held by the sleeves 103A and 103B of the mesh 102. Alternatively, the frame 164 may be constructed of two male and female half frames structured and assembled using any of the methods disclosed hereinabove to form the frame 164 with the first sheet 162 firmly held between the first and second arms 164A and 164B and with the second sheet 168 firmly held between the third and fourth arms 164D and 164E. In addition, embodiments of the four armed implant 164 may be non-tensioned or pre-tensioned, including implant embodiments in which both the first sheet 162 and the second sheet 168 are held under tension, implant embodiments in which the first sheet 162 is held under tension and the second sheet 168 is not held under tension, implant embodiments in which the first sheet 162 is non-tensioned and the second sheet 168 is tensioned and implant embodiments in which both the first sheet 162 and the second sheet 168 are non-tensioned.

It is also noted that further embodiments of the four armed implants of the present invention may include implants in which the proximal ends of the first arm and the second arm are bent at an angle α towards each other as disclosed hereinabove for the implant 140 (of FIG. 29). Furthermore, embodiments of the four armed implants may be implemented as flat implants, but may also be shaped as curved implants in which either the first and second (proximal) arms of the implant are curved, or the third and fourth (distal) arms of the implant are curved, or both the first and second arms and the third and fourth arms of the implant are curved in order to improve the fit of the implant between the vagina 123 and the bladder 110 and urethra 112.

It is noted that in implants embodiments in which the implant frame comprises two half frames as disclosed hereinabove, the female and male half frames may be shaped such that their surfaces facing each other in the frame regions between adjacent connecting members (of the male half frame) or between the recesses (of the female half frame are modified to improve the harnessing of the sheet of the implant between the male and female half frames.

Figure 31:
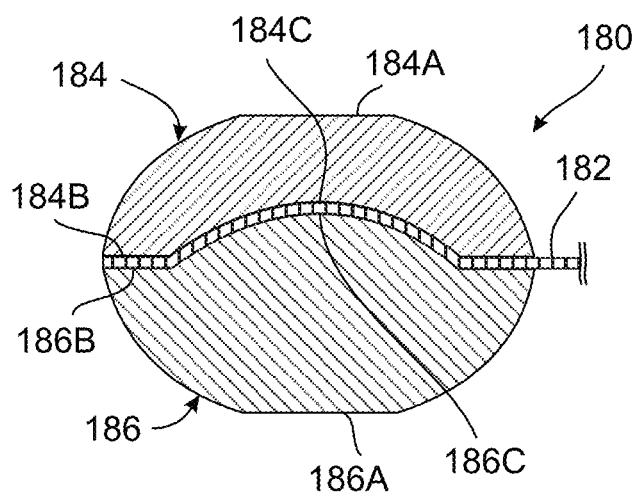
FIG. 31 is a schematic cross sectional view of part of an assembled implant, in accordance with an embodiment of the implants of the present application.

Reference is made to FIG. 31, which is a schematic cross sectional view illustrating part of an assembled implant, in accordance with another embodiment of the implants of the present application. The implant 180 includes a (female) half frame 184 and a (male) half frame 186. The implant 180 also includes a sheet 182. The half frame 184 has an outer surface 184A and an inner surface 184B. The half frame 186 has an outer surface 186A and an inner surface 186B. In the assembled implant 180, the inner surface 186A of the half frame 186 faces towards the inner surface 184B of the half frame 184 and the sheet 2 is disposed between the surfaces 186B and 184B. The half frame 186 has a "bulge" or a protruding portion 186C that may have a semicircular cross-sectional shape. The protruding portion 186 may extend longitudinally along the half frame 186 in the portions thereof lacking any connecting members (such as, for example, protruding members similar to the protruding members 35 of FIG. 8). The half frame 184 has a recessed portion 184C that may have a semicircular cross-sectional shape which is shaped to receive therein the protruding portion 186C when the implant 180 is assembled. The recessed portion 184C may extend longitudinally along the half frame 184 in the portions thereof lacking recesses shaped to receive therein the connecting members of the half frame 186 (such as, for example recesses similar to the recesses 32 of FIG. 5).

When the implant 180 is assembled, the protruding portion 186C is disposed within the matching recessed portion 184C and the sheet 182 is tightly held between the recessed portion 184C and the protruding portion 186C. As substantial portions of the inner surfaces 186B and 184B are convexly and concavely curved, respectively, the contact area between the inner surface 186B and the opposing surface of the sheet 182 is substantially larger as compared to the contact area achievable had the inner surface been planar (and not convexly curved). Similarly, the contact area between the inner surface 184B and the opposing surface of the sheet 182 is substantially larger as compared to the contact area achievable had the inner surface been planar (and not concavely curved). Thus, the arrangement of the curved surfaces (or protruding and recessed surfaces) provides a higher friction between the contacting surfaces of the sheet 182 and the inner surfaces 184B and 186B than the friction that is achievable with flat (planar) surfaces. This configuration of the contact surfaces therefore improves the harnessing of the sheet 182 by the frame of the implant 180 resulting in an augmented gripping of the sheet 182 by the half frames 186 and 184.

It is noted that the specific shape of the surfaces 186B and 184B and the surfaces 186C and 184C illustrated in FIG. 31 is not obligatory. Rather, any type of matching protruding and recessed portions may be used, such as inner surface portions having a protruding and recessed triangular cross sectional shapes, rectangular cross sectional shapes, or any other non planar surfaces of such protruding and matching recessed surfaces may be used in the half frames of the implants of the present application.

It is noted that the present application is contemplates to includes any type of combination of the features and structural components of the implants disclosed in the present application unless they are mutually exclusive or incompatible with each other. For example, the flat implant 20 may or may not include the bent arm portions or parts (such as, for example, bent arms similar to the bent arm portions 144D and 144E of the implant 140) by suitably modifying the proximal ends of the arms of the frame 4. Similarly, the sheet 2 of the implant 20 (FIG. 1) may be a rectangular or nearly rectangular mesh (see, for example, the mesh 132 of the implant 130) and may span only a part of the region circumscribed by the frame 4. Another exemplary modification may include forming a notch (similar to the notch 142A of the mesh 142 of implant 140) in the proximal end of any of the implants 20, 30, 90, 100, 120 and 160, if desired. Thus, any such type of modification of any one of the above disclosed implants by adding (or subtracting) or suitably modifying one or more components of the implant embodiments disclosed herein is included within the scope of the implants of the present application unless they result in physically or structurally incompatible components or unless such modifications are mutually exclusive.

It is further noted that while some exemplary embodiment of the implants disclosed hereinabove use a mesh attached to a frame, any of these embodiments may also use a sheet as defined hereinabove. In such embodiments if a sheet is used, any connecting members which pass through openings in the mesh may pass through suitable openings formed in the perimeter of the sheet, and such openings in the sheet are made in the perimeter of the sheet such that they may be aligned to match the position of the connecting members. Alternatively, some of the implants may use a sheet comprising a contiguous membrane with no openings. For example, in implants having two half frames with protruding connecting members and matching recesses or passages (such as, for example, the implants 30, 50, 60 and 70), the connecting members may punch holes through the contiguous sheet or membrane when the male and female half frames are pressed to each other during the assembly of the implant. The "punching" of such holes in the sheet or membrane by any of such protruding members may simplify the assembly of the implants because it may eliminate the need to precisely align pre-formed holes in the sheet with the protruding connecting members. The feasibility of such a hole punching method may depend, inter alia, on the thickness, strength and other mechanical and thermal properties of the membrane or sheet being used, and may be possible irrespective of the method of attachment being used (such methods may include but are not limited to, thermal bonding, thermal nailing, ironing, ultrasonic welding, and suitable mechanical "ball and socket" type or "snap in" methods, as disclosed hereinabove).

A method for treating bladder prolapse is described with reference to FIGS. 28-30. A patient is set up for surgery, placed in a gynecological position, and anesthetized. A weighted speculum is placed in the lower vaginal wall to expose the prolapsed upper vaginal wall. An incision is made along the center of the upper wall of the vagina 123. In a preferred embodiment, the incision is approximately 1 mm deep and 4 cm long. Using a sharp instrument such as a scissor, the vagina 123 is separated from the bladder wall through the initial incision. Alternatively, the vagina 123 may be separated from the wall of the bladder 110 using blunt dissection—such as with the tip of a finger. These types of incisions and separations are well-known in the art, and the methods of the present invention are not limited to the details included herein. An implant (such as, for example, the implant 120 of FIG. 28) may be compressed and inserted through an incision in the vagina 123 and situated between the vagina 123 and the bladder 110. The implant 120 may then expanded into its fully relaxed state (if the implant is a non-tensioned implant) or into its partially relaxed state (if the implant is a pre-tensioned implant as disclosed hereinabove), wherein the arms 124A and 124B are situated close to the pelvic sidewalls (not shown) alongside the Arcus Tendenius Pelvis Fascia (not shown) without tension or with gentle tension holding it in place. The vaginal incision is then sutured closed under the implanted implant 120. As shown in FIG. 28, the implant 120 is situated between the vagina 123 and the bladder 110, supporting the bladder 110 and preventing it from descending (prolapsing) onto the vaginal canal.

In an alternative embodiment, an incision is made between the vagina 123 and the rectum (not shown), and device 120 is inserted into a position that provides support of the rectum (not shown), with the frame compressed against a para-rectal compartment (not shown). In this embodiment, the implant 120 would be similar in shape, but generally different in size than device 120 used for bladder support.

Returning to FIG. 29, in an alternative embodiment, if the implant 140 is used, the bent arm portions and the notch 142A in the mesh 142 may be positioned adjacent the cervix 117 to improve support.

Turning to FIG. 30, in an alternative embodiment if the implant 164 is implanted in a patient, the first sheet 162 is placed between the vagina 123 and the bladder 110 and supports the bladder 110 and the second (strap-like) sheet 168 held by the third and fourth arms 164C and 164D is placed between the wall of the vagina 123 and the urethra 112. This arrangement is particularly advantageous in cases of patients in which POP is combined with SUI since the support of the second sheet 168 improves support of the urethra 112 and may therefore reduce or eliminate urine leakage in cases of SUI.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is noted that any of the implants disclosed in the present application may also be used for the treatment of hernia of the abdominal wall, or diaphragmatic hernia, or inguinal hernia by suitably modifying or adapting the shape and/or dimensions, and/or curvature or any other parameter of the implant to fit the type of treatment, such modifications will be apparent to the person skilled in the art and are therefore not disclosed in detail herein.

It is also noted that in accordance with additional embodiments of the implants of the present application, the arms of the frame of the implant may be configured as several types of arms. For example, any of the first and the second arm of the implants may be configured an articulated arm or a segmented arm, or an arm formed as an integral part of the frame, or an arm that is attached to said frame. Such articulated or segmented arms may enable more freedom in shaping the implant during implantation. In attached arms, the arms may be formed as a separate part of the frame and may be attached to the frame of the implant when the frame is assembled by using any attachment type known in the art, including but not limited to a ball and socket type of attachment mechanism, a screw-like attachment mechanism, gluing, ultrasonic welding, thermal welding or any other suitable type of attachment mechanism or attachment method known in the art.

Similarly, if the implant is of the type that has four arms (such as the exemplary implant 160 of FIG. 30), any of the first arm, second arm, third arm and fourth arm may be configured as an articulated arm or a segmented arm or an arm formed as an integral part of said frame or an arm that is attached to said frame, as disclosed hereinabove. For example, in an implant of the type illustrated in FIG. 30, if the third and fourth arm may be attachable arms that may be attached to the implant at any stage of the assembly of the implant. This type of attachable arm may be useful in cases in which the first sheet of the implant (such as, for example, the first sheet 162) needs to be attached to the first arm 164A and the second arm 164B before the second sheet (such as, for example the second sheet 168) is attached to the third and fourth arms 164C and 164D. In such a case, the first sheet 162 may be first attached to the first arm 164A and the second arm 164D by using any of the attachment methods disclosed hereinabove and after the first sheet 162 is attached to the arms 164A and 164B (either under tension or without being under tension), the third and fourth arms (such as for example the arms 164C and 164D) of the implant may be attached to the implant by any suitable method of attaching or mechanism for attachment as disclosed in detail hereinabove.

It is further noted that in implants having four arms (such as for example the implant 160), the first sheet and the second sheet of the implant need not necessarily be attached to the arms using the same attachment method. For example, in an embodiment of the implant, the first sheet 162 may be attached to the first and second arms using ultrasonic welding, while the second sheet 168 may be attached to the third and fourth arms by inserting the third and fourth arms 164C and 164D into sleeves formed in the second sheet, as disclosed in detail hereinabove and illustrated in FIG. 24. In another embodiment of the implant, the first sheet 162 may be attached to the first and second arms 164A and 164B by using the sheet attachment method and the arm configuration disclosed in detail with respect to the implant 130 of FIGS. 25 and 26 while the second sheet 168 may be attached to the third and fourth arms 164C and 164D by ironing. It is therefore noted that in the implants having four arms of the present application any of the attachment methods disclosed hereinabove may be used for attaching the first sheet of the implant to the first and second arm of the implant and any of the attachment methods disclosed hereinabove may be used for attaching the second sheet of the implant to the third and fourth arm of the implant. Any possible combination and permutation of attachment methods of the first and second sheets of the same implant and of the arms' structure and configuration may be possible and may be practiced in the implants of the present application.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is noted that while the novel method of thermal bonding disclosed hereinabove was demonstrated for use in pelvic implants, it is by no means limited to such specific implants. Rather, the method may be generally applies to any implant requiring securing a sheet or mesh to a supporting frame of any shape by thermal bonding methods such as ultrasonic welding. In a non-limiting example, the method may be used for constructing breast implants usable for breast shape reconstructive surgery and for any other types of surgical implants including a sheet or a mesh held by a frame.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treatment of a patient having a pelvis, the method comprising:
   a. providing a device comprising: (i) a first sheet having a first perimeter and a second sheet having a second perimeter; and (ii) a frame for holding said first sheet at a portion of said first perimeter, and for holding said second sheet at a portion of said second perimeter wherein said frame comprises a first arm, a second arm, a third arm and a fourth arm,
   wherein said first arm and said second arm hold said first sheet along at least a portion of said first perimeter and wherein said third arm and said fourth arm hold said second sheet along at least a portion of said second perimeter,
   b. implanting the device into the patient such that:
   A. said first sheet is implanted in said pelvis between a vagina of said patient and a bladder of said patient; and
   B. said second sheet is implanted to be disposed between said vagina and a neck of said bladder of said patient and/or an urethra of said patient.

2. The method of claim 1 wherein neither the first arm nor the second arm are part of a closed loop.

3. The method of claim 2 wherein:
   (A) each of said first, second, third and fourth arms respectively have a respective base and a respective tip;
   (B) the base of said first arm is co-located with the base of said third arm; and
   (C) the base of said second arm is co-located with the base of said fourth arm.

4. The method of claim 3 wherein neither the third arm nor the fourth arm are part of a closed loop.

5. The method of claim 1 wherein neither the third arm nor the fourth arm are part of a closed loop.

6. The method of claim 5 wherein:
   (A) each of said first, second, third and fourth arms respectively have a respective base and a respective tip;
   (B) the base of said first arm is co-located with the base of said third arm; and
   (C) the base of said second arm is co-located with the base of said fourth arm.

7. The method of claim 1 wherein:
   (A) each of said first, second, third and fourth arms respectively have a respective base and a respective tip;
   (B) the base of said first arm is co-located with the base of said third arm; and
   (C) the base of said second arm is co-located with the base of said fourth arm.

\* \* \* \* \*